Figure 1B:
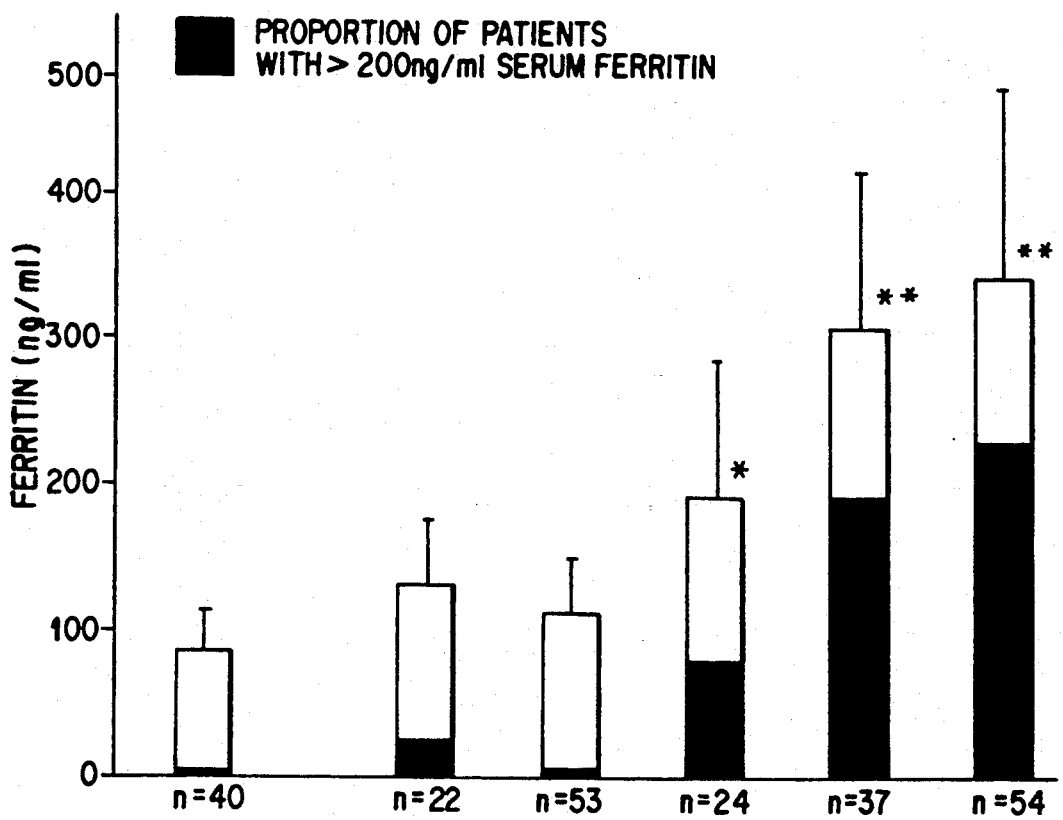

United States Patent [19]

Moroz et al.

[11] Patent Number: 5,120,640
[45] Date of Patent: Jun. 9, 1992

[54] PLACENTAL ISOFERRITINS FOR THE PROGNOSIS AND DIAGNOSIS OF IMMUNOSUPPRESSION

[76] Inventors: Chaya Moroz, 40 Yehuda-Hanasi St, Tel-Aviv, Israel, 69393; Sol L. Misrock, 74 Hilltop Dr., Chappaqua, N.Y. 10514

[21] Appl. No.: 689,656

[22] Filed: Apr. 23, 1991

Related U.S. Application Data

[63] Continuation of Ser. No. 164,947, Mar. 7, 1988, abandoned, Continuation-in-part of Ser. No. 148,133, Jan. 22, 1988, Pat. No. 4,882,270, which is a continuation of Ser. No. 568,275, Jan. 4, 1984, which is a continuation-in-part of Ser. No. 373,715, Apr. 30, 1982.

[51] Int. Cl.⁵ ............................................ G01N 33/577
[52] U.S. Cl. .................................... 435/7.1; 435/7.92; 435/7.94; 435/240.26; 435/240.27; 436/536
[58] Field of Search ................... 435/5, 7.1, 7.92, 7.94, 435/240.26, 240.27; 436/536, 813

[56] References Cited

U.S. PATENT DOCUMENTS 4,278,652  7/1981  Niemann et al. ............... 436/801 X

FOREIGN PATENT DOCUMENTS 1201667  3/1986  Canada.

OTHER PUBLICATIONS

Moroz, C., et al., Cancer, 54 No1: 84–89 (1984).
Blumberg, B., et al., Lancet 1:347 (1984).
Moroz C., et al., Clin Chim Acta 148: 111–118 (1985).
Matzner et al., 1989, Am. J. Hematol. 9:13–22 ("Matzner et al., 1980").
Moroz and Kupfer, 1981, Israel J. Med. Sci. 17:879–881 ("Moroz and Kupfer").
Bezwoda et al., 1985, Scand. J. Haematol. 35:505–510 ("Bezwoda et al.").
Matzner et al., 1985, Br. J. Haematology 59:443–448 ("Matzner et al., 1985").

*Primary Examiner*—Christine Nucker
*Assistant Examiner*—Jeffrey Stucker
*Attorney, Agent, or Firm*—Pennie & Edmonds

[57] ABSTRACT

Methods for diagnosis and prognosis of immunosuppressive conditions are disclosed, involving the detection of a particular isoform of ferritin, placental ferritin (PLF), in patient samples such as sera or on peripheral blood lymphocytes. PLF is elevated in immunosuppressed patients at early stages of disease; by contrast, adult insoferritins are elevated at late stages of immunodeficiency. Depending upon the nature of the disease associated with the immunodeficiency, the elevated levels of PLF detected at early stages may remain elevated or diminish as disease progresses. Examples are described in which elevated levels of PLF were detected at very early stages of of HIV-infection. The elevated levels diminished as disease progressed from ARC to AIDS. By contrast, adult isoforms of ferritin became elevated at late stages of disease.

9 Claims, 8 Drawing Sheets

PLACENTAL ISOFERRITINS FOR THE PROGNOSIS AND DIAGNOSIS OF IMMUNOSUPPRESSION

This is a continuation of application Ser. No. 164,947, filed Mar. 7, 1988, now abandoned.

The present application is a continuation-in-part of copending application Ser. No. 143133, now U.S. Pat. No. 4,882,270 filed Jan. 22, 1988, issued Nov. 21, 1989, which is a continuation of application Ser. No. 568,275 filed Jan. 4, 1984, which is a continuation-in-part of application Ser. No. 373,715 filed Apr. 30, 1982 claiming priority under 35 U.S.C. §119 to Israel Application Ser. No. 62879 filed May 15, 1981, each of which is incorporated by reference herein in its entirety.

TABLE OF CONTENTS

1. Introduction
2. Background of the Invention
3. Summary of the Invention
    3.1. Definitions
4. Description of the Figures
5. Detailed Description of the Invention
    5.1. Placental Ferritin and Monoclonal Antibodies Specific for Placental Ferritin
        5.1.1. The molecular Heterogeneity of Placenta Ferritin
        5.1.2 The Subunit Structure of Placenta Ferritin Reactive with H9 and G8 McAbs
        5.1.3. Enzymatic Digestion of Placenta Isoferritin with V8 Protease
    5.2. Detection of Placental Ferritin
    5.3. Placental Ferritin and Immunosuppressive Conditions
        5.3.1. Placental Ferritin and HIV Infection
6. Preparation of Monoclonal Antibodies Specific for Placental Ferritin
    6.1. Preparation of Placental Ferritin
    6.2. Preparation of Monoclonal Antibodies that Bind to Placental Ferritin
        6.2.1. Materials and Methods
        6.2.2. Immunization Protocol
        6.2.3. Spleen Cell-Myeloma Fusion
        6.2.4. Screening Protocols
    6.3. Preparation of Monoclona Antibodies Specific for Placental Ferritin and Not Cross Reactive with Normal Ferritin
        6.3.1. Immunization and fusion Protcols Antibody CM-H9
        6.3.2. Characterization of Monoclonal Antibody CM-H9
    6.4. Immunoassays for Lymphocyte-Bound Placental Ferritin Using CM-H9 Monoclonal Antibody
        6.4.1. Collection of Lymphocytes
        6.4.2. Radioimmunoassay Procedures
        6.4.3. Cytotoxic Assay Procedure
        6.4.4. Results: Reactivity of CM-H9 Monoclonal Antibody with Lymphocytes in Certain Diseases
7. Isoferritins in HIV Infection: Relation to Clincal Stage, CD8+ Lymphocyte Binding and the Pathogenesis of AIDS
    7.1. Materials and Methods
        7.1.1. Materials and Methods
        7.1.2. Isolation of Lymphocytes
    7.1.3. Monoclonal Antibodies
        7.1.4. Flow Cytometry and Immunofluorescence Staining
        7.1.5. Immunofluorescence Staining of Isoferritin on Lymphocyte Membranes Using CM-H9 McAb
        7.1.6. Immunofluorescence Staining of Isoferritin in Lymphocyte Cytoplasma Using CM-H9 McAb
        7.1.7. Levamisole Treatment of Mononuclear Cells
        7.1.8. Quantitative Determination of Serum Isoferritin
        7.1.9. Statistical Analyses
    7.2 Results
        7.2.1. Serum Levels of Ferritin and PLF in Patients with HIV Infection
        7.2.2. Relationship of High Serum PLF and Normal Ferritin to Disease Progression
        7.2.3. Cell Surface Antigens of Lymphocytes from HIV Infected Patients
        7.2.4. The effect of Levamisole on Cell Surface Antigens or Lymphocytes from HIV Infected Patients
8. Isoferritins in Patients with Lymphoproliferative Diseases
    8.1 Materials and Methods
        8.1.1. Subjects
        8.1.2. Monoclonal Antibodies
        8.1.3. Quantitative Determinations of Ferritin
        8.1.4. Monoclonal Antibody ELISA For PLF and Common Isoferritins
    8.2 Results
        8.2.1. Evaluation of Liver Ferritin Standard by Different ELISAs
        8.2.2. Binding of Placenta and Liver Ferritins to CM-G8 and CM-H9 McAbs
        8.2.3. Isoferritins in the Serum of Healthy Individuals and Patients with Lymphoproliferative Diseases
9. Isoferritins in Autoimmune Conditions
10. Deposit of Hybridoma

1. INTRODUCTION

The present invention relates to methods for the diagnosis and prognosis of immunosuppressive conditions. The method of the invention involves the detection of placental ferritin (PLF) in patient samples such as serum, or on peripheral blood lymphocytes. Elevated levels of PLF are detected in patients at early stages of immunosuppression. Depending upon the nature of the disease associated with the patients, immunosuppressed condition, the elevated PLF levels may decline with progression of disease. The detection and measurement of PLF may be accomplished using monoclonal antibodies described herein.

The invention is demonstrated by way of examples in which elevated PLF was detected in sera of subjects infected with human immunodeficiency virus (HIV). Individuals at early stages of disease exhibited the highest PLF levels which declined as the disease progressed.

2. BACKGROUND OF THE INVENTION

Ferritin is an iron storage protein which maintains iron in an available, non-toxic form. A variety of ferritin isoforms have been isolated from different tissues. The variability of ferritin characteristics appear to be mainly caused by the presence of different subunit types in the multimeric protein shell (Drysdale, 1977, Ciba Found. Symp. 51:41; Arosio, et al., 1978, J. Biol. Chem. 253:4451; Watanabe et al., 1981, Biochem. Biophys.

Res. Comm. 103:207). In fact, three ferritin subunits have been described. The L subunit (19 Kd), prevalent in iron loaded tissues, the H subunit (21 Kd), predominant in iron poor and malignant cells (Drysdale, 1977, supra; Arosio, 1978, supra) and the glycosylated G subunit (24 Kd) isolated from serum (Cragg et al., 1981, Biochem. J. 199:565). Different isoferritins contain different proportions of L and H subunit types. More recently, preliminary analysis of cDNA clones revealed that the H and L subunits are encoded by rather complex families of genes (Brown et al., 1983, Proc. Natl. Acad. Sci. USA 73:857; Costanzo et al., 1984, EMBO J. 3:23), suggesting that the heterogeneity of ferritin molecules may be even greater than presently determined.

Various ferritin isoforms have been isolated from normal and malignant tissues, the most acidic ones predominating in tumor and fetal tissues (Drysdale, 1976, Ciba Found. Symp. 51:41; Arosio et al., 1978, J. Biol. Chem. 253:4451). It has been suggested that the assay of acidic isoferritin in the serum may be of value in the diagnosis of malignancy (Hazard et al., 1977, Nature 265:755). Elevated concentrations of serum ferritin were found in patients suffering from a variety of malignant diseases, including acute lymphocytic leukemia (ALL) (Matzner et al., 1980, Am. J. Hematol. 9:13), hepatoma (Giannoulis, 1984, Digestion 30:236), breast cancer (Jacobs et al., 1976, Br. J. Cancer 34:286), and recently Hodgkin's disease (Bezwoda et al., 1985, Scand. J. Haematol. 35:505). In assays based on antibodies against HeLa cell ferritin, Hazard and Drysdale found higher concentrations of ferritin in sera from patients with various tumors than in the same sera assayed by antibodies directed against normal liver ferritin (Hazard, et al., supra.). Others have failed to demonstrate a consistent pattern of isoferritins in tumor tissues (Cragg et al., 1977, Br. J. Cancer 35:635; Halliday et al., 1976, Cancer Res. 36:4486) or in sera obtained from patients with tumors (Jones et al., 1978, Clin. Chim. Acta. 85:81; Jones et al., 1980, Clin. Chim. Acta. 106:203). There are, therefore, conflicting views as to the origin and specificity of the elevated serum ferritin in malignant diseases.

3. SUMMARY OF THE INVENTION

The present invention is directed to a method for the diagnosis and prognosis of immunosuppressive conditions involving the detection of a particular isoform of ferritin, placental ferritin (PLF), in patient samples such as sera or on peripheral blood lymphocytes. The method of the invention is based, in part, on the surprising discovery that PLF (and not other isoferritins) is elevated in immunosuppressed patients at early stages of disease. Depending upon the nature of immunosuppressed patient's disease, the levels of PLF may remain elevated or may diminish as the disease advances. By contrast to PLF, adult isoferritin levels are elevated at late stages of immunodeficiency. This discovery was made possible, in part, by the development of monoclonal antibodies such as CM-H9 described herein (and in related parent applications) which bind to PLF exclusive of other ferritins such as the liver and spleen isoforms. These monocolonal antibodies enabled the detection of patients' levels of PLF exlusively, during the course of disease. In accordance with the invention, monoclonal antibodies exhibiting this type of specificity can be used in immunoassays to monitor levels of PLF in patient samples. Such PLF profiles can be used in the diagnosis and prognosis of immunosuppression.

3.1. DEFINITIONS

| | |
|---|---|
| AIDS = | acquired immune deficiency syndrome |
| ARC = | AIDS-related complex |
| BSA = | bovine serum albumin |
| CD4 = T4 = | marker of helper/inducer T lymphocytes |
| CD8 = T8 = | marker of cytotoxic/suppressor T lymphocytes |
| CD2 = T11 = | marker of total T cell population, sheep erythrocyte rosette receptor |
| ELISA = | enzyme linked immunosorbent assay |
| HIV = | human immunodeficiency virus; HTLV-III; LAV |
| McAb = | monoclonal antibody(ies) |
| PBS = | phosphate-buffered saline |
| PLF = | placental isoferritin (also referred to as oncofetal ferritin) |
| SD = | standard deviation |

4. DESCRIPTION OF THE FIGURES

FIG. 1 The mean serum levels of PLF (A) and normal ferritin (B) measured simultaneously in HIV infected patients and in healthy blood bank donors. n=number of subjects tested. The bars represent mean +1 SD (standard deviation). (*) represents values significantly higher than in blood bank donors by t-test $p<0.01$; xx, $p<0.001$.

Figure 2:
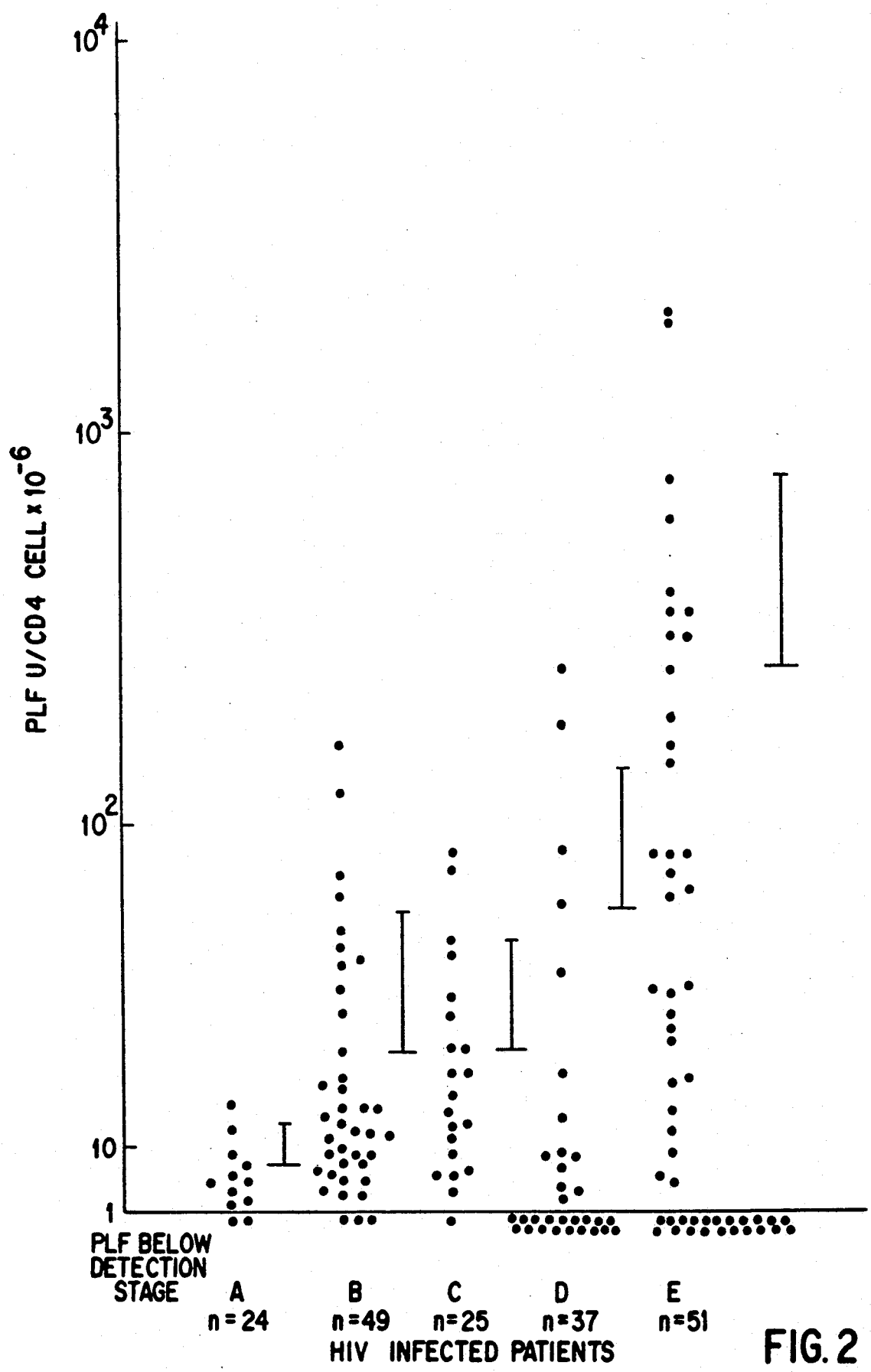

FIG. 2. The ratio of serum PLF per $CD4^+$ lymphocyte of HIV infected patients. The bars represent mean +1 SD.

Figure 3:
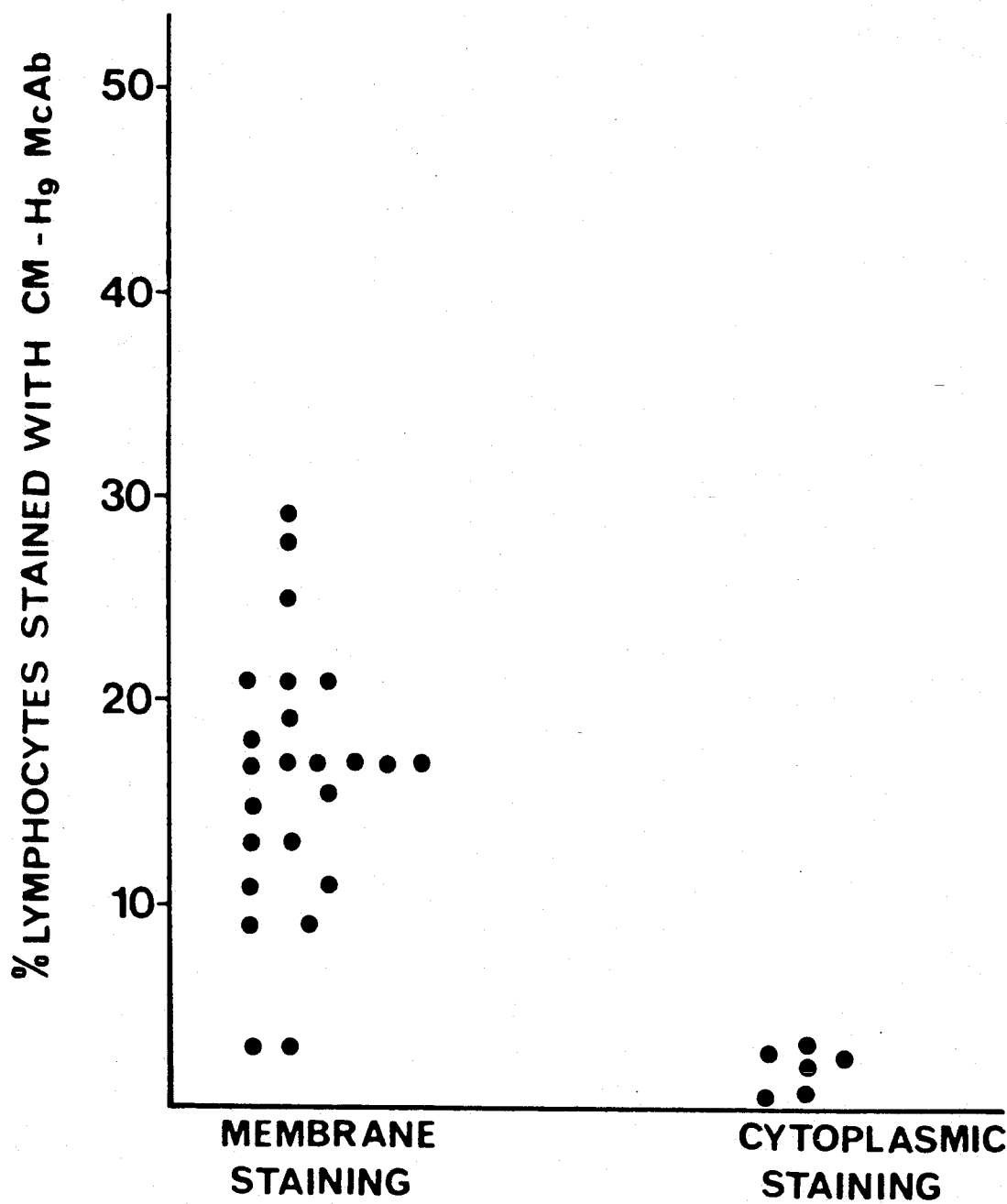

FIG. 3. Scattergram of the percentage of circulating lymphocytes positively stained for PLF with CM-H9 McAb, in HIV infected patients from categories A-E. Each point represents the determination in a single patient.

Figure 4:
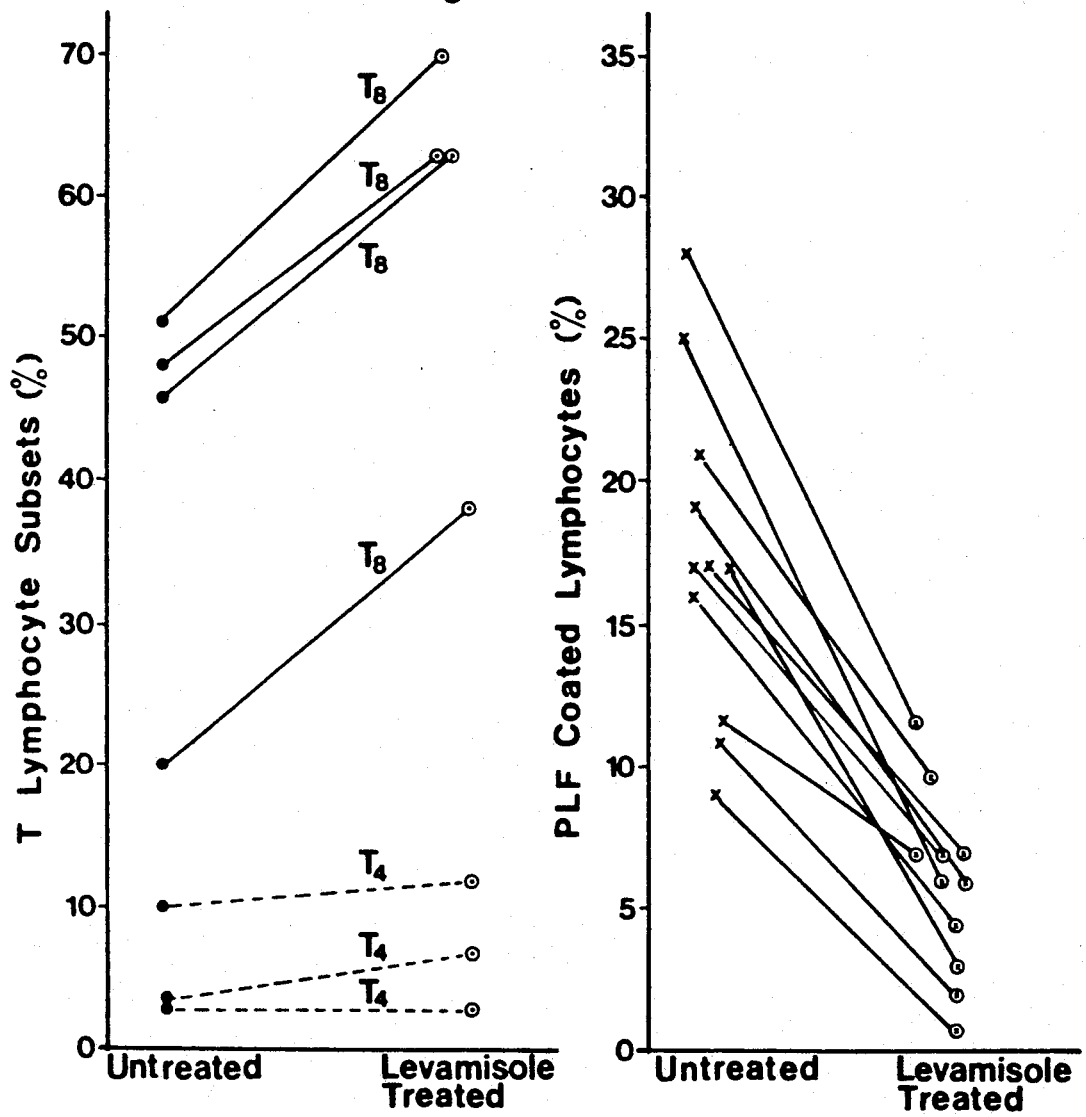

FIG. 4. The effect of levamisole treatment of lymphocytes from HIV infected patients on the detectable number of $T4^+$, $T8^+$, and $PLF^+$ cells Lymphocytes were incubated in vitro with levamisole (40 $\mu$g/ml) or with medium (in untreated cells), for 30 minutes at 37° C. prior to incubation with the conjugated McAbs.

Figure 5:
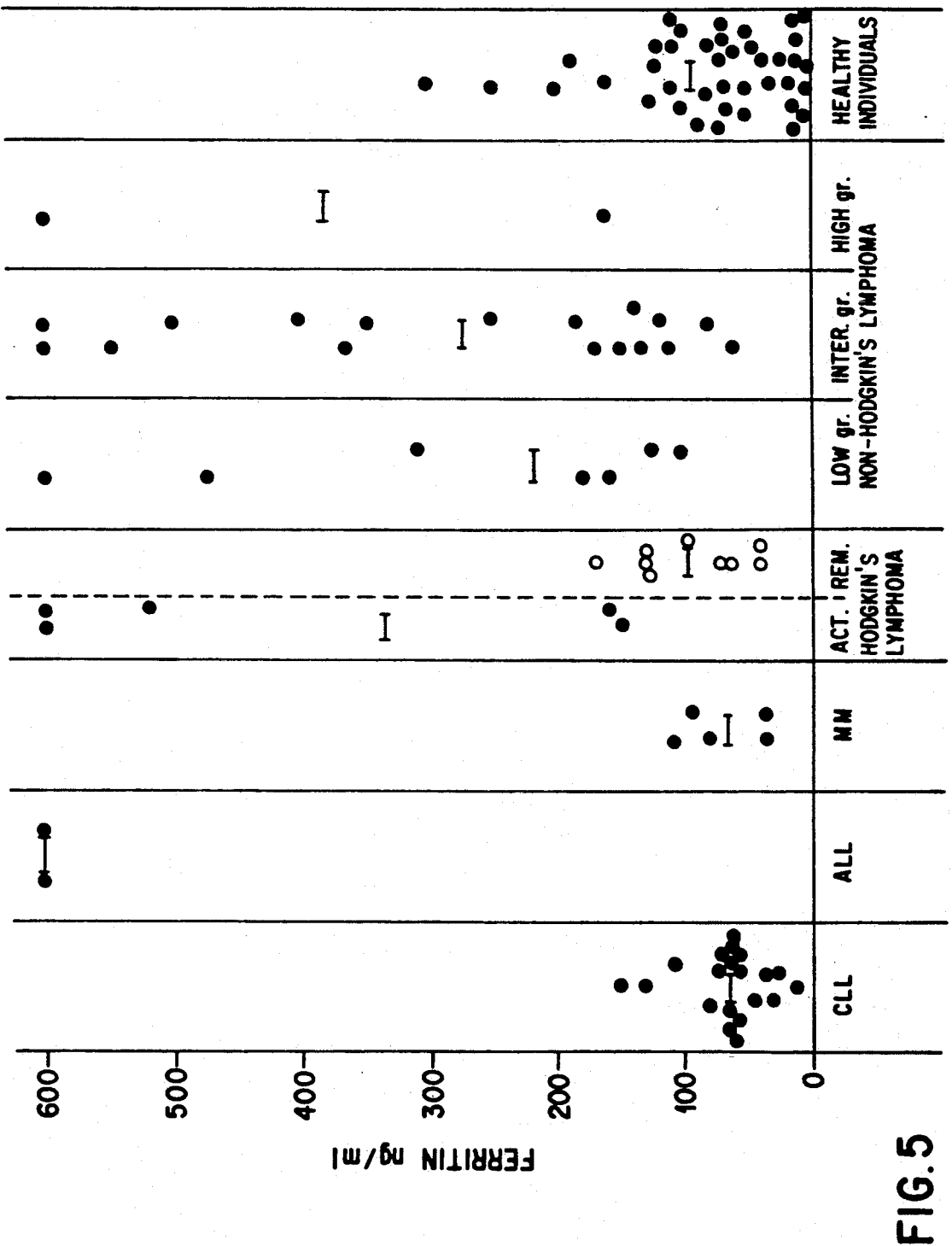

FIG. 5. Scattergram illustrating the total serum ferritin level in patients with hematologic malignancies (first seven columns) and in healthy individuals (right column). Total ferritin was measured by McELISA type A using liver ferritin as standard.

Figure 6:
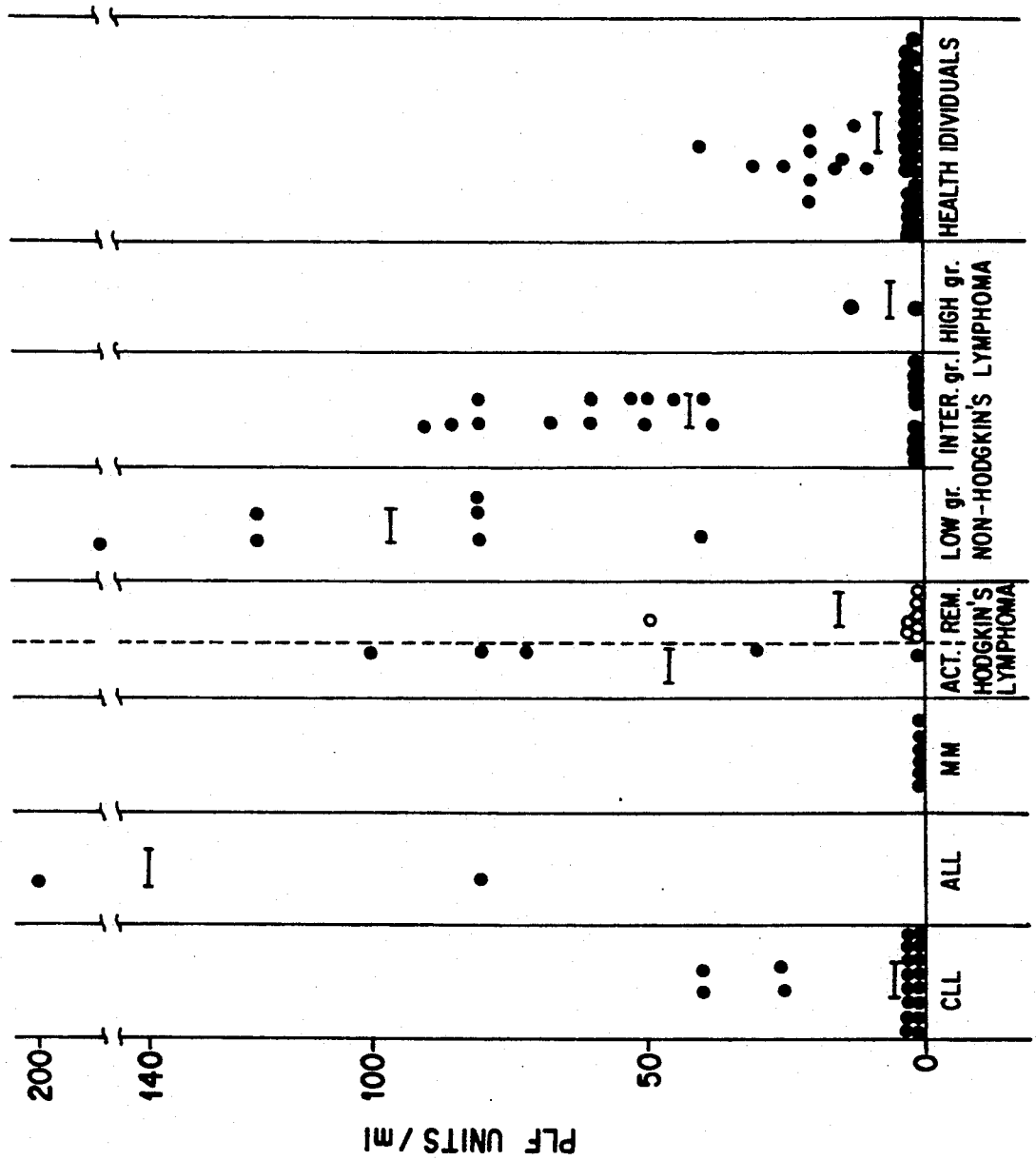

FIG. 6. Scattergram exhibiting serum PLF levels in patients with hematologic malignancies (first seven columns) and in healthy individuals (right column). PLF was measured by McELISA type B using placental ferritin as standard.

Figure 7A:
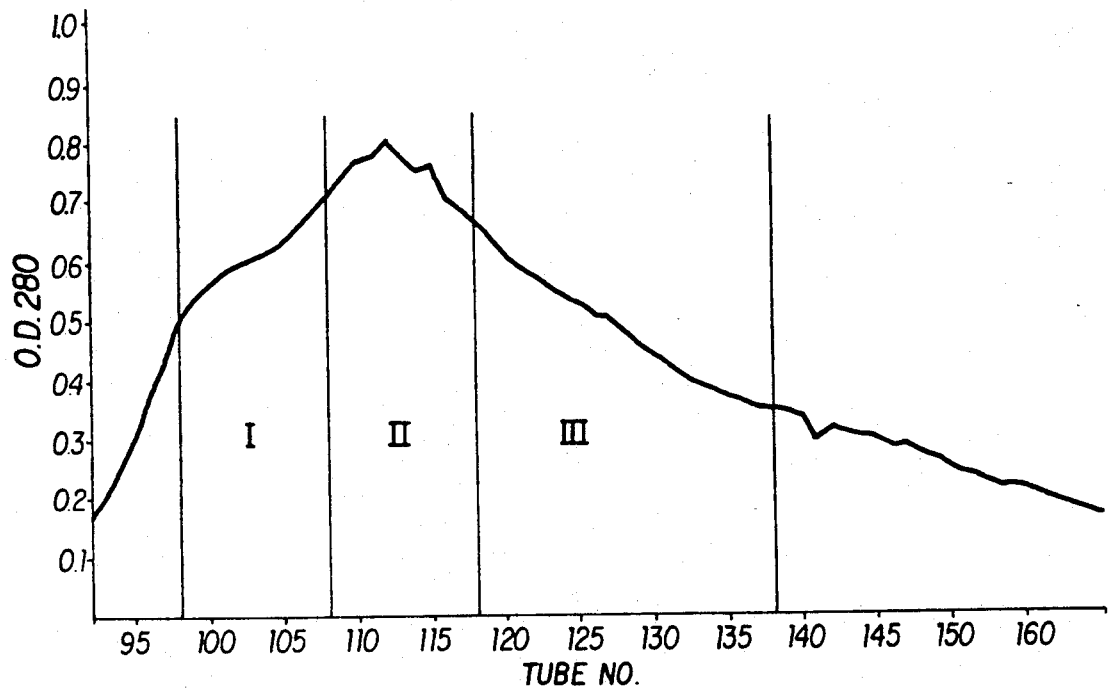

FIG. 7A. Elution profile of PLF. Placental ferritins were prepared as described, infra, and PLF was eluted from a DEAE-cellulose column using a Tris-HCl (pH 7.5) gradient of 0.02M to 0.05M.

Figure 7B:
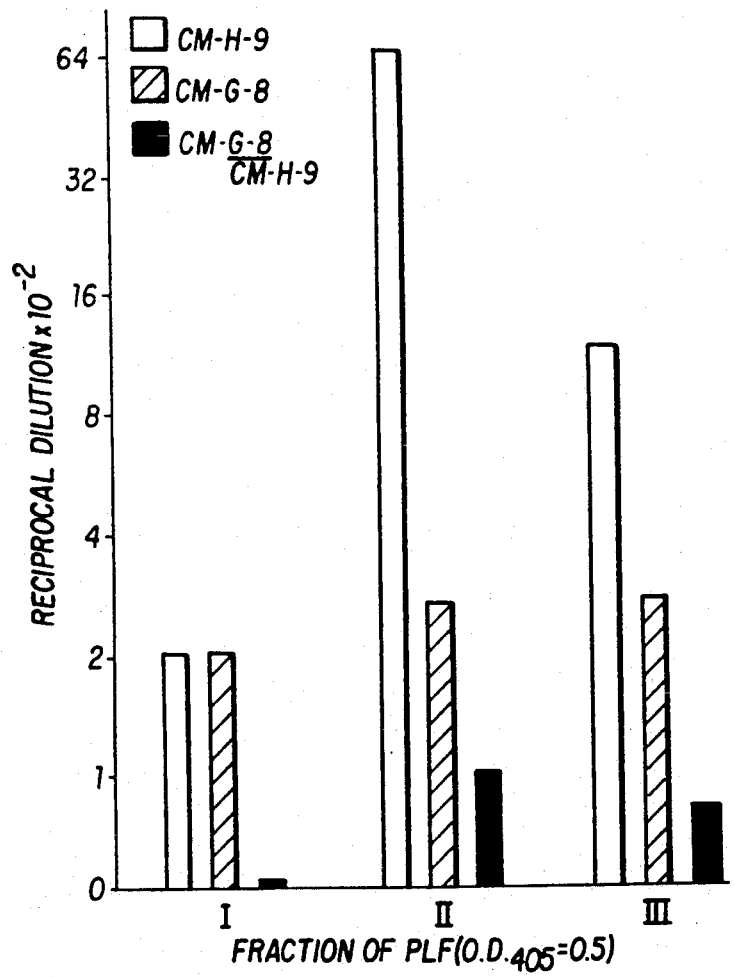

FIG. 7B. The content of PLF in each fraction as assayed by ELISA. The following capture/detection antibodies were used in ELISA sandwich assays: CM-H9 capture/CM-H9 detection; CM-G8 capture/CM-G8 detection; and CM-G8 capture/CM-H9 detection.

Figure 8:
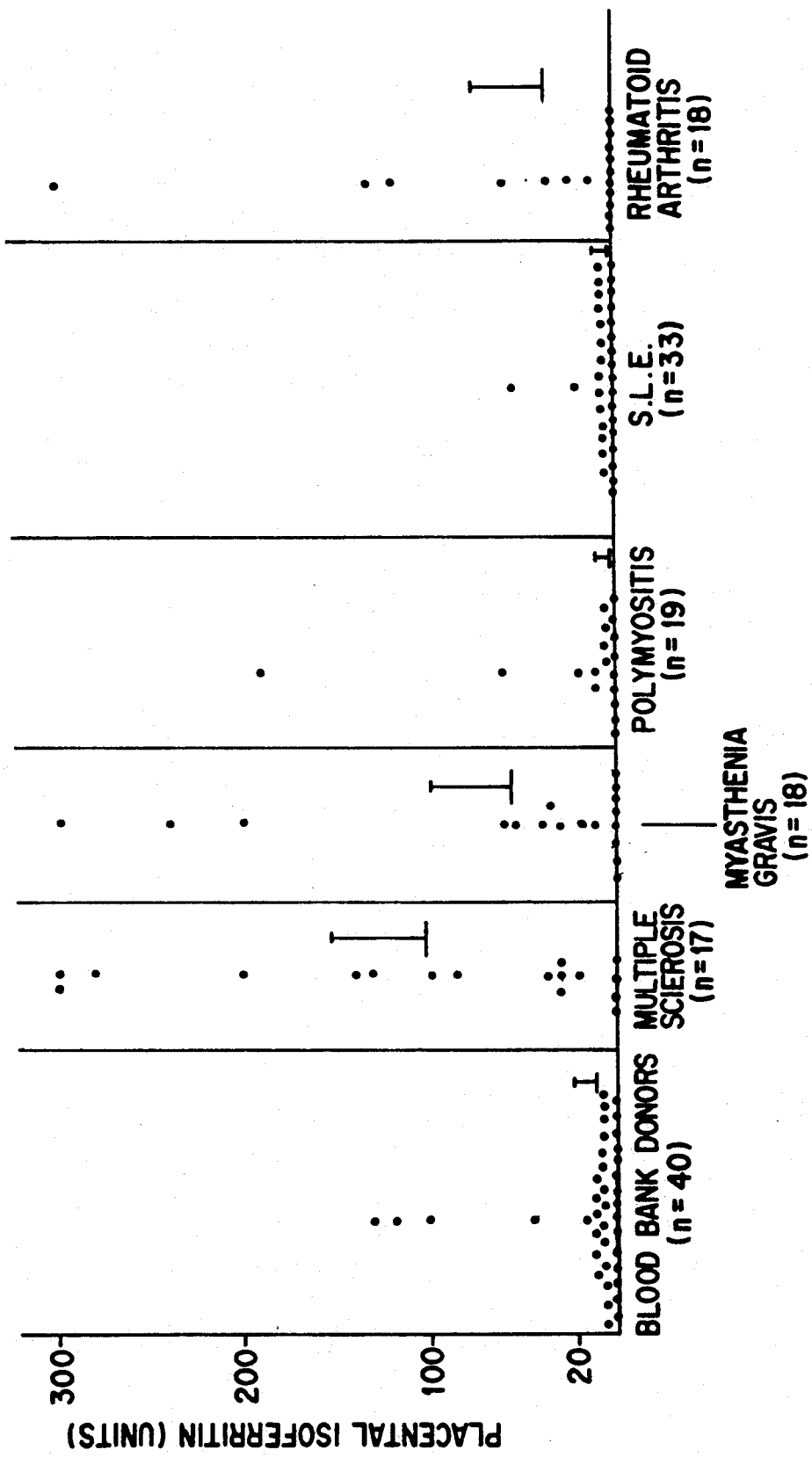

FIG. 8. Scattergram of PLF levels detected in patients with autoimmune diseases. PLF levels are elevated in those diseases which are characterized by immunosuppression.

5. DETAILED DESCRIPTION OF THE INVENTION

The present invention relates to methods for the diagnosis and prognosis of immunodeficient or immunosuppressive conditions which may be caused by any of a number of diseases or agents. For example, immunosuppression which occurs with acquired immunodeficiency syndrome (AIDS) caused by HIV infection, certain lymphomas and leukemias as well as certain autoimmune conditions such as rheumatoid arthritis, myasthenia gravis, multiple sclerosis and the like may be diagnosed and staged using the methods of the invention.

The invention is based, in part, upon the surprising discovery that PLF (placental ferritin), as opposed to isoforms of adult ferritin, is elevated in immunosuppressed patients at early stages of disease. Depending upon the nature of the immunosuppressed patient's disease, the levels of PLF may remain elevated or may diminish as the disease advances. By contrast to PLF levels, adult ferritin is elevated at late stages of immunodeficiency. This discovery was made possible, in part, by the development of a monoclonal antibody, CM-H9 (described herein and in parent applications) which is specific for PLF and does not cross react with adult ferritin.

In accordance with the invention, measurement of PLF levels in patient samples can be used for the early diagnosis of immunosuppression. Moreover, the monitoring of both PLF and normal adult ferritin levels can be used prognostically to stage the progression of immunosuppression. Although a variety of tissues can be tested for the presence of PLF and/or adult ferritin, serum and peripheral blood lymphocytes (PBL) are convenient test samples. While adult ferritin can be assayed in serum (and in various tissues of the body) PLF occurs not only in serum but also appears to bind to the surface of a particular subset of circulating lymphocytes. Thus, when PLF is first produced at very early stages of disease, the circulating lymphocyte subset may bind all the available PLF so that the serum levels of PLF may appear to be normal, while the circulating lymphocytes will test positive for PLF. However, as increasing amounts of PLF are produced during early stages of immunosuppression, the subset of lymphocytes which bind to PLF will become "saturated" at which point elevated serum levels of PLF should be detected.

Depending upon the nature of the immunosuppressed patient's disease, PLF levels may remain elevated or may decrease as the disease progresses. For example, in HIV-infected patients, PLF levels are elevated at early stages of disease, yet diminish at late stages of disease. By contrast, in patients with lymphoproliferative diseases such as Hodgkins lymphoma, non-Hodgkins lymphoma of low and intermediate grades, as well as patients with acute lymphocytic leukemia (ALL), PLF levels are elevated at early stages of disease and remain elevated as disease progresses. While the applicants are under no duty or obligation to explain the mechanism of the invention, it may be that the infected lymphocytes in the case of AIDS or the malignant lymphocytes in the case of lymphoma and leukemia are the cellular sources of the PLF which is expressed at elevated levels per cell during immunosuppression. Accordingly, in AIDS patients, as the population of infected lymphocytes declines, the levels of PLF detected will diminish. By contrast, in lymphoma and leukemia as the population of malignant lymphocytes proliferate, the levels of PLF will remain elevated.

The detection of PLF in patient samples may be accomplished by any of a number of methods. A convenient approach for detecting PLF, as described in more detail infra, involves immunoassays that utilize monoclonal antibodies which define and bind to PLF exclusive of isoforms of adult ferritin. Such monoclonal antibodies may be used in any immunoassay format for the detection of PLF, including but not limited to, enzyme-linked immunosorbant assays (ELISA), radioimmunoassays, fluorescent immunoassays, etc. in a "sandwich" or competition format or cytotoxic assay systems. In specific embodiments described herein, two types of monoclonal antibodies are described which are particularly useful in a sandwich immunoassay format: one monoclonal antibody cross reacts with both PLF and adult ferritin, whereas a second monoclonal antibody specific for PLF does not cross react with adult ferritin. The cross-reactive antibody can be used in a sandwich immunoassay as a "capture antibody" to capture all isoforms of ferritin present in the sample, e.g., both PLF and adult ferritin. The PLF-specific monoclonal antibody can be labeled and used to detect captured PLF whereas the cross-reactive monoclonal antibody can be labeled and used to detect all captured isoforms of ferritin.

The subsections below describe the characterization of PLF, monoclonal antibodies that define PLF and the diagnostic and prognostic uses of PLF in autoimmune conditions. The invention is demonstrated by way of examples in which levels of serum PLF and adult ferritin in HIV infected patients as well as patients with lymphoma or leukemia and certain autoimmune diseases were monitored during the course of disease using monoclonal antibodies for PLF and adult ferritin in an ELISA sandwich format.

5.1. PLACENTAL FERRITIN AND MONOCLONAL ANTIBODIES SPECIFIC FOR PLACENTAL FERRITIN

Two monoclonal antibodies, CM-H9 which reacts exclusively with PLF, and CM-G8 which cross reacts with both PLF and adult ferritin, were used to characterize placental ferritin. Placental ferritin(s) reactive with CM-H9 was most acidic in comparison to CM-G8 reactive molecules, indicating structural heterogeneity in human placenta ferritin. A three subunit structure of placenta ferritin was revealed by our analysis: an 18 Kd light (L) subunit and 20 Kd heavy (H) subunit as well as a 43 Kd subunit. The 18 Kd L and 20 Kd H subunits have been shown previously for spleen and liver ferritins; however, the third high molecular weight subunit (43 Kd) seems to be unique for human placenta ferritin. CM-H9 reactive placental ferritin was composed only of the 43 Kd subunit. This 43 Kd subunit could not be further dissociated under exhaustive reducing conditions.

The 43 Kd unique subunit of human placenta ferritin so identified appears to be either part of the ferritin molecule or associated with it. This notion is based on the findings that this subunit contains the CM-G8 reactive antigenic epitopes present in spleen and liver ferritin. Furthermore, CM-H9 relative ferritin contained measurable amount of iron as was evident by its reactivity with potassium ferrocyanide and +T8+and PLF+cells Lymphocytes were may therefore be considered as a placenta associated isoferritin. Using CM-H9 and CM-G8 to analyze fractions of PLF eluted from a DEAE column revealed that the 43 Kd subunit can occur as a homopolymer or as a dimer with the L or H chain.

Some structural similarities between the 20 Kd H subunit and the 43 Kd subunit were observed. Both subunits were sensitive to V8 proteolysis and both lost their antigenic reactivity with CM-G8 following SDS treatment under reducing conditions. It may be that the high molecular weight subunit (43 Kd) of placenta ferritin is either a stable dimer or precursor of H subunit (20 Kd) (See also, Parhami-Seren and Moroz, 1986, G.I. Pat. Clin. 1(1):17).

Finally, the unique 43 Kd subunit present in placenta ferritin which reacts with CM-H9 was also found in ferritin molecules synthesized by breast cancer cells and not in ferritin synthesized by normal breast cells. Furthermore, CM-H9 reactive ferritin was detected in blood of breast cancer patients but not in healthy individuals. We therefore suggest that the CM-H9 reactive 43 Kd subunit is characteristic of carcino fetal ferritin.

5.1.1. THE MOLECULAR HETEROGENEITY OF PLACENTA FERRITIN

Placenta ferritin obtained following DEAE-cellulose chromatography (as described in Section 6.1 infra) was subjected to isoelectric focusing (IEF), and was further reacted with either $^{125}$I-CM-H9 or $^{125}$I-CM-G8 McAb. $^{125}$I-CM-H9 McAb reacted with placenta ferritin at pH ranging from 4.7-5.2. On the other hand, spleen ferritin isoelectrofocused on agar, did not react with $^{125}$I-CM-H9 McAb. $^{125}$I-CM-G8 McAb reacted with placenta ferritin focused at pH 5.1-5.4, and with spleen ferritin focused at pH of 5.4-5.5. The results of IEF indicate that placental ferritin is heterogeneous. The most acidic ferritin (pI 4.7-5.0), reacted with CM-H9 McAb whereas the less acidic molecules (pI 5.1-5.2) reacted with both CM-H9 and CM-G8 McAbs. It was also found that spleen ferritin focused at pH 5.4-5.5 reacted with $^{125}$I-CM-G8 McAb whereas no reactivity was observed with $^{125}$I-CM-H9 McAb at such pH.

The PLF fractions eluted from the DEAE-cellulose column (as described in Section 6.1, infra) were further analyzed by ELISA assays using the following capture/detection antibodies: (a) CM-H9 capture/CM-H9 detection; (b) CM-G8 capture/CM-G8 detection; and (C) CM-G8 capture/CM-H9 detection. Results shown in FIG. 7A and 7B demonstrate the relative quantities of the different PLFs in these fractions. Matzner et al., (1985, Brit. J. Haematol. 59:443-448) reported that Fraction II demonstrates the greatest biological activity (i.e., immunosuppressive effect on T cell function in vitro) whereas Fraction I, does not demonstrate such activity. Interestingly, our results reveal that the more active Fraction II contains the greatest amount of CM-H9 reactive PLF.

5.1.2. THE SUBUNIT STRUCTURE OF PLACENTA FERRITIN REACTIVE WITH CM-H9 AND CM-G8 MONOCLONAL ANTIBODIES

Separation of placenta ferritins by SDS-PAGE under reducing conditions followed by immunoblotting with $^{125}$ICM-H9 or $^{125}$ICM-G8 revealed that $^{125}$ICM-H9 reacted with a single subunit structure (43 Kd) of placental ferritin. No reactivity of $^{125}$ICM-H9 McAb was observed with spleen ferritin. No reactivity with $^{125}$ICM-G8 McAb could be observed with placenta or spleen ferritin. These results determinants of both placenta and spleen were sensitive to SDS treatment under reducing conditions. Further immunoblotting experiments were carried out with polyclonal rabbit anti-human spleen ferritin and $^{125}$I-protein A. A single band of 18 Kd was evident in both placenta and spleen ferritin following SDS-PAGE.

Since CM-G8 reactive determinants of both placenta and spleen ferritins could not be detected following SDS treatment, experiments were designed in which affinity purified placenta ferritin was radiolabeled and immunoprecipitated with the monoclonal antibodies prior to SDS-PAGE. $^{125}$ICM-H9 reactive ferritin immunoprecipitated with different concentrations of CM-H9 McAb and electrophoresed on SDS-PAGE revealed a single subunit structure of 43 Kd. This subunit structure was not further dissociated following exhaustive reducing conditions (boiling for 10 minutes in 2% SDS and 5% β-mercaptoethanol or in 6M urea). On the other hand, $^{125}$ICM-G8 reactive ferritin immunoprecipitated with different concentrations of CM-G8 McAb and subjected to SDS-PAGE, under the above described conditions exhibited three distinct subunits of 43, 20 and 18 Kd. These results indicate the presence of a 43 Kd subunit structure common to both CM-H9 and CM-G8 reactive ferritins, whereas only the CM-G8 reactive ferritin contained, in addition to the 43 Kd subunits, the H and L chains.

5.1.3. ENZYMATIC DIGESTION OF PLACENTA ISOFERRITIN WITH V8 PROTEASE

Further experiments were carried out to determine the sensitivity of the ferritin subunits to limited proteolysis by V8 protease. Most of the 43 Kd subunit of CM-H9 reactive ferritin was digested following a 60 minute incubation with V8 protease. However, a complete digestion of this subunit was not achieved even following incubation for 120 minutes. When CM-G8 reactive ferritin was treated with V8 protease, the 43 Kd as well as the 20 Kd subunits were completely digested.

5.2. DETECTION OF PLACENTAL FERRITIN

A convenient method for the detection of PLF in patient samples involves immunoassays that utilize monoclonal antibodies which define PLF exclusive of isoforms of adult ferritins. Such antibodies may be configured in a variety of immunoassays including, but not limited to ELISA, radioimmunoassays, fluorescent immunoassays, etc. in a "sandwich", competition, or cytotoxic/target cell format.

In specific embodiments described herein, two types of monoclonal antibodies are described which are particularly useful for such assays: monoclonal antibodies such as CM-G8, which cross react with both PLF and adult ferritin, and monoclonal antibodies such as CM-H9, which are specific for PLF and do not cross react with adult ferritin. These antibodies may be used in a number of configurations in a sandwich type assay to monitor both PLF and adult ferritin levels in a patient. For example, a PLF specific antibody can be used as both the capture and detection antibody to monitor levels of PLF. Alternatively, a cross-reactive antibody can be used to capture all isoforms of ferritin (i.e., both PLF and adult ferritin) in the sample; in this case, a PLF specific antibody can be used to detect the PLF isoforms in the sample, and a cross- reactive antibody can be used on a duplicate sample to detect all cross reactive ferritins present in the sample. The results of such a sandwich assay can provide a profile of the relative levels of PLF and adult ferritin in a patient sample.

In another embodiment of the invention, the PLF and cross-reactive antibodies may be differentially labeled and used to determine the relative proportions of PLF and adult ferritin in a sample. In such applications, each antibody may be labeled with a different fluor, chromophore, photoemitter, or enzyme to produce a different fluorescent or colorimetric signal. The measurement of each signal could provide for a differential analysis of PLF and adult ferritin in a single sample.

The immunoassays of the invention are not limited to the use of CM-H9 and CM-G8 monoclonal antibodies. In fact, other monoclonal antibodies which are functionally equivalent to CM-H9 and CM-G8 are contemplated for use in accordance with the invention. To this end, CM-H9 and CM-G8 can be used to isolate the respective PLF and adult ferritin molecules in order to produce functionally equivalent antibody molecules that can be used in accordance with the invention. Such monoclonal antibodies can be prepared using any techniques which provides for the production of antibody molecules by continuous cell lines in culture. For example, the hybridoma technique originally developed by Kohler and Milstein (1980, Sci. Am. 243(4): 66–74) as well as other techniques which have more recently become available, such as the human B-cell hybridoma technique (Kozbor et al., 1983, Immunology Today 4:72) and the EBV-hybridoma technique to produce human monoclonal antibodies (Cole et al., 1985, Monoclonal Antibodies and Cancer Therapy, Alan R. Liss, Inc., pp. 77–96) and the like are within the scope of the present invention. Antibody molecules produced by such methods which define the CM-H9 and CM-G8 epitopes (e.g., those that competitively inhibit the binding of CM-H9 or CM-G8 to their target antigens) would be selected for use in accordance with the invention.

The present invention, however, is not limited to the use of monoclonal antibody molecules for the detection of PLF. As more or different methods for the isolation and characterization of PLF are developed, it will become apparent to the skilled artisan that such techniques could also be used in accordance with the invention to monitor patient samples for PLF.

5.3 PLACENTAL FERRITIN AND IMMUNOSUPPRESSIVE CONDITIONS

The results presented in the Examples infra are discussed below. In particular, the data presented in Section 7 demonstrate that PLF is produced in HIV-infected patients, and that the presence of PLF could play a significant role in the pathogenesis of immunodeficiency in AIDS. The data presented in Sections 8 and 9 demonstrate that PLF levels are elevated in patients with certain lymphomas and leukemias and autoimmune diseases that are characterized by immunosuppression.

The availability of a distinct monoclonal antibody which specifically defines PLF, enabled us to design an assay to measure serum levels specifically of PLF, independently of the amount of adult ferritin. From these measurements, isoferritin profiles were derived which may serve as prognostic indicators for the progression of HIV seropositive patients to ARC and to AIDS.

5.3.1. PLACENTAL ISOFERRITIN IN HIV INFECTION

PLF was measured in patients classified by the following stages: Stage A, HIV seropositive but no clinical manifestations or physical findings; Stage B, lymphadenopathy and/or splenomegaly; Stage C, clinical symptoms or findings related to ARC; Stage D, Kaposi's sarcoma, lymphoma, or CNS (central nervous system) disease without systemic opportunistic infections; and Stage E, opportunistic infections originally defined by the CDC as diagnostic of AIDS. The results reveal that the majority of HIV infected patients with early clinical manifestations (Stage B), exhibit significant elevations in the concentration of serum PLF. These elevations are maintained in most patients at Stage C (ARC). In contrast, further progression of the disease into AIDS is accompanied by a significant elevation in the level of total serum ferritin, but by a diminution in PLF concentration. The increase in normal ferritin levels in AIDS patients has been previously reported by other investigators (Blumberg, B., et al., 1984, Lancet 1:347; Gupta, S., et al., 1986, J. Clin. Lab. Immunol. 20:11–13).

Although the Applicants are under no duty to explain the invention, we suggest that in HIV infected individuals, the increase in serum PLF is closely associated with the development of lymphadenopathy and later clinical manifestations of AIDS-related complex. Increases in the level of normal ferritin appear to be associated predominantly with the progression of the disease from ARC to AIDS. Subjects with clinically latent HIV infection (stage A) do not show rises in serum isoferritins.

The cellular origin of the serum PLF in HIV infected patients is not yet known. However, the observation that with the progression of the disease, decreases in the serum level of PLF positively correlated with decreases in the total number of CD4+ lymphocytes, suggests that PLF may originate from these CD4+ cells. Indeed, both serum PLF levels and the total number of CD4 lymphocytes decrease during disease progression. However, the proportion of HIV infected CD4+ lymphocytes within the diminishing population increase in the proportion of HIV infected CD4+ lymphocytes may explain the observed increase in the ratio of serum PLF concentration per individual CD4+ lymphocyte in stage E (FIG. 2). These results suggest that serum PLF originates from the HIV infected CD4+ cells, and that therefore, the ratio of serum PLF levels per CD4+ lymphocyte may be used as a diagnostic indicator of the degree of infection. In sum, while the highest absolute concentrations of serum PLF were associated with early stage HIV infection, the ratio of the concentration of PLF per circulating CD4+ lymphocyte may be useful as an index of the degree of cellular infection.

The results also demonstrated that in HIV infected subjects, there exists a subset of CD8+ cells (15.2±6.4%) to which PLF is bound, masking the CD8 antigen. It is unclear whether the receptor for PLF is the CD8 antigen, or a site close to it such that CD8 is masked by PLF via steric hindrance. Since the majority of CD8+ lymphocytes were neither PLF-positive nor blocked in their reaction with McAb-T8, the former possibility seems very unlikely. The masking of a T cell surface receptor by isoferritin derived from tumors has been observed in cancer patients (Hann, H. W. L., et al., 1984, Nature (London) 265:755–756; Moroz, C., et al., 1977, Clin. Exp. Immunol. 29:30–35; Moroz, C., et al, 1977, N. Engl. J. Med. 296:1175; Moroz, C., et al., 1977, Cancer Immunol. Immunother. 3:101-104; Moroz, C., et al., 1984, Cancer 54:84-89). In these patients, isoferritin inhibited E-rosette formation by the masked T cells. In AIDS patients, the E-receptor (T11 antigen) was not masked when tested with anti-T11 McAb. The discrepancy between the above observations may lie in the ligands used to identify the E-receptor.

It is perhaps significant that the surface PLF was removed by treatment of HIV infected lymphocytes with levamisole, but not by parallel incubation in complete tissue culture medium. The incubation with levamisole resulted in unmasking of the normal CD8 surface marker. This observation is compatible with previous findings on the unblocking effect of levamisole on lymphocytes from patients with Hodgkin's disease and breast cancer (Moroz, C., et al., 1977, Cancer Immunol. Immunother. 3:101-104; Ramot, B., et al., 1976, N. Engl. J. Med. 294:809). Levamisole has been shown to act as an immunopotentiating drug (Levo, Y., et al., 1975, Biomedicine 23:198-200; Nekam, K., et al., 1981, Immunopharm. 3:31-40) yet its mode of action is not yet understood.

The pattern of isoferritin expression across the clinical spectrum of HIV infection suggests that PLF may play a role in the pathogenesis of progressive immunodeficiency, as it appears to do in the pathogenesis of Hodgkin's disease. A small proportion of peripheral blood lymphocytes of normal subjects (up to 6-7%) both in the present study and in prior analyses (Moroz, C., et al., 1984, Cancer 54:84-89), most likely within the CD8 pool, binds PLF. This population appears to be expanded in HIV infected patients. In addition, serum PLF rises dramatically in relatively early HIV infection, corresponding to the period of maximal lymphoid activation in clinical stages B and C. Preliminary data from Walker et al. (1986, Science 234:1563-1566) suggests that certain CD8 lymphocytes can inhibit HIV proliferation in vitro. Hypothetically, PLF could inhibit the immunocompetence of these CD8 cells, thereby contributing to the progressive expression of HIV that is characteristic of late-stage disease (id.).

An explanation for the rise of PLF early in HIV infection, followed by a decrease later in infection, is so far lacking. One possibility, supported by our preliminary data, is that trans-activating viral gene (tat III) products increase PLF mRNA expression in virus-infected CD4 cells. The depletion in the total number of these cells late in AIDS could explain the observed declines in serum PLF concentration, during which time total ferritins increase in response to nonspecific stimuli (e.g., secondary infection) as acute-phase reactants.

The finding that levamisole, a known immunopotentiator, enhances the elution of PLF from a CD8+ subset might indicate a role for this drug in the therapy of HIV infections, particularly if used in early stages of the disease.

6. PREPARATION OF MONOCLONAL ANTIBODIES SPECIFIC FOR PLACENTAL FERRITIN

The subsections below describe the preparation of placental ferritin and monoclonal antibodies (e.g., CM-H9 McAb) that define a unique epitope of placental ferritin (PLF). These antibodies do not cross react with spleen or liver ferritin.

6.1. PREPARATION OF PLACENTAL FERRITIN

Placental ferritin was prepared from human placenta by a modification of the method used by Beamish et al. (1971, J. Clin. Path. 24:581). Placental tissue (500 g) was sliced and water added to a total volume of 2000 ml. After homogenization the tissue suspension was heated to 75° C. for 20 minutes. The supernatant, after cooling and centrifugation at 10,000 rpm for 15 minutes, was treated with acetic acid to bring the pH to 4.6. The precipitated protein was removed by centrifugation at 10,000 rpm for 15 minutes and a clear supernatant was adjusted to neutral pH with dilute NaOH. When the clear brown supernatant was ultracentrifuged at $100,000 \times g$ for 240 minutes the suspended ferritin collected in a small button at the bottom of the tube. The precipitate was redissoved in 0.9% saline and further purified by passage through a Sephadex G200 column. The ferritin fraction from this column was passed through a DEAE cellulose anion exchange resin using Tris-HCl buffer at pH 7.5 and a 0.02-0.5 M gradient. Three protein peaks were obtained, the most acidic peak $pI = 4.8$ was collected and used for analysis. Its purity was shown by isoelectric focusing and immunoelectrophoresis against anti-ferritin serum and anti-human whole serum. This protein was used for the immunization of mice as described below.

6.2. PREPARATION OF MONOCLONAL ANTIBODIES THAT BIND TO PLACENTAL FERRITIN

The following protocol was used to produce monoclonal antibodies that bind to PLF but which may also cross react with other isoferritins. The protocol and monoclonal antibodies made are described in the following applications: U.S. Pat. No. 4,882,270, filed Jan. 22, 1988, issued Nov. 21, 1989 a continuation of application Ser. No. 568,275 filed Jan. 4, 1984, a continuation in part of application Ser. No. 373,715, filed Apr. 30, 1982 which claims priority to Israel application Ser. No. 62879, filed May 15, 1981, each of which is incorporated by reference herein in its entirety. See also, Moroz et al., 1985, Clinica Chemica Acta 148:111-118.

6.2.1. MATERIALS AND METHODS

The following media and solutions were used in the preparation of the monoclonal antibodies:
a. RPMI-O (No FCS)
b. RPMI 1640-HY
500 ml sterile distilled water
55 ml 10×RPMI-1640
6 ml 1.0 N Sodium Hydroxide
14 ml 7.5% Sodium Bicarbonate
6 ml Pen/strep)
10 ml Glutamine)+DMEM
86.5 ml FCS)
c. RPMI-HY-HATD-day 0 to day 7 For 100 ml of medium
95 ml RPMI −1640+20% FCS
1.0 ml Pyruvate (100×)
2.0 ml 50×HAT
2.0 ml 50×deoxycytidine
d. RPMI—HY—HT—day 8 to day 14
For 100 ml of medium
97 ml RPMI-1640+20% FCS
2.0 ml 50×HT
1.0 ml Pyruvate (100×)

For Hybrids from day 15/onwards use RPMI-1640+20% FCS and pyruvate, or maintain in RPMI-HY-HT.

e. PEG 33 and 25% w/v

Must be ordorless and white. For 100 ml autoclave relevant wt in grams in a glass bottle at 15 lbs for 10-15 minutes. When bottle is cool enough to hand hold (about 50° C.) add RPMI 1640-0 to make up to 100 ml, swirl to mix, store at room temperature.

f. HATD—Final concentrations of reagents

H = Hypoxanthine $10^{-4}$M
A = Aminopterin $10^{-6}$M
T = Thymidine $2 \times 10^{-5}$M
D = Deoxycytidine $2 \times 10^{-6}$M
HT Stock 100x — 100 cc
Thymidine (M.W. 242.33): 0.04846 g
Hypoxanthine (M.W. 136.1): 0.1361 g.
Add $H_2O$ up to 100 ml and warm to 60°-70° C. to dissolve. Readjust final volume with double distilled water (dd $H_2O$). Dilute to 50×, sterile filter (0.2μ) and store 2 ml aliquots at −20° C.

g. A Stock 1000× — 100 cc
Aminopterin (F.W. 440.4): 0.44 g
Bring to 50 ml with dd $H_2O$, add 0.1 N NaOH dropwise until aminopterin dissolves. Bring final volume to 100 ml with dd $H_2O$. Adjust volume to 100 ml. Sterile filter (0.2μ) and store at −20° C..

h. D Stock 100× — 100 cc
Deoxycytidine (M.W. 227.2): 0.00454 g
Dissolve in dd $H_2O$, adjust to 100 cc, dilute to 50x stock. Sterile filter (0.2μ) and store at −20° C.

i. HAT−50× −200 ml
Combine 100 ml 100×HT with 10 ml 1000×A +90 ml dd $H_2O$ = 50×HAT. Sterile filter (0.2μ) and store 2 ml aliquots at −20° C.

6.2.2. IMMUNIZATION PROTOCOL

Balb/c female mice (4-6 weeks old initially) were immunized with 3 weekly inoculations of 50 μg acidic placental ferritin (prepared as described in Section 6.1, supra) in complete Fruends adjuvant. Hybridizations were performed 3 days after the last injection of 10 μg acidic placental ferritin. Hyperimmune mice were rested at least one month before the final boost.

6.2.3. SPLEEN CELL-MYELOMA FUSIONS

Spleen cells were prepared as follows:
a. Spleens were removed from mice in RPMI-O;
b. Rinsed 2× in petri dish with RPMI-O;
c. Teased apart in RPMI-O with 18 ga. needles;
d. Cell suspension transferred to a tube and large chunks of tissue settled out;
e. Single cell suspension removed to a new tube spun at 800 RPM (160×g) 5 min; Red blood cells lysed with 0.83% NH Cl, pH 7.5;
f. Cells washed 3× with RPMI-O, resuspended in same;
g. Cells counted with Trypan Blue.

Myeloma cells used for fusion, PB/NS1/1-Ag4-1 were grown in RPMI-1640 with 20% Fetal Calf Serum (FCS) and prepared as follows:
a. Myeloma cells were removed from culture flasks with gentle pipetting into 50 ml Falcon/Corning tube;
b. Spun down at 900 RPM (200×g) 5 minutes;
c. Washed 1× with RPMI-O, resuspended in same and counted with Trypan Blue.

Spleen cells were fused to the myeloma cells as follows:
a. Spleen and myeloma cells were combined in a 10:1 ratio in a single 50 ml conical Falcon/Corning disposable centrifuge tube;
b. Cells were pelleted at 900 RPM (200×g) for 5 minutes;
c. Medium was aspirated as completely as possible;
d. All solutions and media used from now on were at room temperature; centrifuge tube with cell pellet was immersed in a bath at 37° C., and the following was added accompanied by gentle stirring: 0.2 ml 33% PEG 1500 for 1 minute, centrifuged at 200×g for 5 minutes. Cells were resuspended and stirred gently for 1 minute followed by the addition of 5 ml RPMI-O gentle stirring and addition of 5 ml RPMI-O 20% Fetal Calf Serum. Hybrid mixture looked like a poorly resuspended cell suspension at this point with many small clumps;
e. The mixture was pelleted at 200×g 5 minutes;
f. Cells were resuspended in RPMI-HY-HATD (at 37° C.) at a concentration of $3 \times 10^6$/cc by squirting medium onto the cell pellet;
g. Hybrids were plated out in flat bottom 96 well plates by adding 2 drops of cell suspension from a 5 ml pipet or with multi-pipettor using cut off tips (about 65 microliters), containing 100-120 RPMI-HY-HATD (approx. $2 \times 10^5$ cells);
h. Control wells containing NS-1 cells+RPMI-HY-HATD at $1 \times 10^6$/ml were set up;
i. Plates were cultured for 7 days;
j. On Day 8 and twice a week thereafter, half of the culture medium was removed by careful aspiration and fed with 80-100 microliters of RPMI-HY-HT medium;
k. Positive wells were screened for at 3 and 4 weeks after hybridization.

6.2.4. SCREENING PROTOCOLS

Screening and determination of the specificity of the monoclonal antibodies was performed by a hemagglutination test. Embryonic placenta and adult spleen ferritin were coupled to Ox red blood cells Ox RBC by $CrCl_2$. 50 μl of increasing dilutions (starting at 1:10 of hybridoma culture medium supernatant were mixed with 10 μl of adult of embryonic ferritin Ox RBC and hemagglutination determined.

Supernatants of clones giving a hemagglutination titer of at least 1:1000 were selected. A clone, designated CM-OF-3 was selected (hereinafter referred to as CM-3). The clone CM-3 produces a monoclonal antibody which is specific for embryonic ferritin and it cross-reacts with both adult and embryonic ferritin.

Another clone, designated CM-G8, produces a monoclonal antibody which binds to placental ferritin and cross reacts with spleen and liver ferritin. CM-G8 defines the same epitope recognized by CM-3.

6.3. PREPARATION OF MONOCLONAL ANTIBODIES SPECIFIC FOR PLACENTAL FERRITIN AND NOT CROSS REACTIVE WITH NORMAL FERRITIN

The following protocol was used to prepare monoclonal antibodies that were specific for PLF and which did not cross react with other isoferritins. In particular, the monoclonal antibody, CM-3 described above was used to block the crossreactive determinants of fetal and adult ferritin, in order to produce a different monoclonal antibody, CM-H9, which is directed to a specific fetal determinant.

6.3.1. IMMUNIZATION AND FUSION PROTOCOLS

The following immunization and fusion procedure was used to obtain monoclonal antibodies that define a unique epitope of PLF and do not cross react with other isoferritins. Embryonic ferritin isolated from human placenta (the protein of pI 4.8 isolated as described in Section 6.1 supra) was reacted with moroclonal antibodies CM-3 in the following ratio: embryonic ferritin (90 μg in PBS) was mixed with Ascites fluid from BALB/c mouse containing CM-3 antiferritin monoclonal antibodies (10 mg/ml).

The mixture was incubated for 30 minutes at 37° C. followed by overnight incubation at 4° C. The mixture was centrifuged at $10,000 \times g$, the precipitate formed was discarded, and the supernatant was used for immunization. Each BALB/c mouse was immunized with the above supernatant mixed with complete Fruend's adjuvant, injected intradermally once a week for 3 weeks. A booster immunization of one fifth of the above dose was injected intraperitoneally.

After 3 days from boost, mouse spleen was aseptically removed and fusion was performed by incubating $10^8$ spleen cells with $10^7$/P3-NSI/1-Ag4 myeloma cells as set out above, designated as CM-OF-H9 (hereinafter referred to as CM-H9) was obtained.

6.3.2. CHARACTERIZATION OF MONOCLONAL ANTIBODY CM-H9

The CM-H9 monoclonal antibody belongs to the IgG class; it does not form precipitates with ferritin, it binds rabbit complement. In the ascitic fluid obtained, the antibody content was about 7 mg per ml. One ml of ascitic fluid binds about 2 mg of placental ferritin and none of adult spleen or liver ferritin.

6.4. IMMUNOASSAYS FOR LYMPHOCYTE BOUND PLACENTAL FERRITIN USING CM-H9 MONOCLONAL ANTIBODY

Monoclonal antibody, CM-H9, can be used in immunoassays for the detection of PLF in test samples such as serum or PLF bound to circulating peripheral blood lymphocytes (PBL). The presence of PLF can be determined by using CM-H9 in any type of immunoassay system, including but not limited to ELISA, radioimmunoassay or cytotoxic assays (where cellular targets are involved).

In general, the assay for the detection of placental ferritin which is bound to peripheral blood lymphocytes may be carried out by (a) isolating lymphocytes from peripheral blood, and (b) determining the presence of PLF on the lymphocytes using a conventional type of assay based on the use of the novel monoclonal antibodies, specific for PLF.

According to a perferred embodiment the test may be carried out as follows:
a. Lymphocytes are isolated from peripheral blood by Ficoll-Hypaque gradient centrifugation;
b. The presence or absence of PLF bound to the surface of the lymphocytes is determined by any conventional type of assay, such as ELISA, cytotoxic test or radioimmunoassay.

6.4.1. COLLECTION OF LYMPHOCYTES

Lymphocytes are collected as follows:

(a) Collect 15 ml blood into a heparin-containing blood collection tube; dilute 1:2 in PBS pH 7.2
(b) Underlay the cell suspension with 10 ml Ficoll-Hypaque density solution (1.077 gm/ml).
(c) Centrifuge for 30 minutes at $300 \times g$ at room temperature.
(d) Collect mononuclear cells from the medium:-Ficoll-Hypaque interface using a Pasteur pipette and transfer to a new 15 ml tube.
(e) Wash cells 3 times by suspension in 15 ml wash medium (PBS, pH 7.2) and centrifuge at $300 \times g$ for 10 minutes at 4° C.
(f) Resuspend in wash medium and determine cell number.

6.4.2. RADIOIMMUNOASSAY PROCEDURES

Two procedures were followed for radioimmunoassay:

A. Radio-Immuno Assay—1

Peripheral blood mononuclear cells were isolated by Ficoll-Hypaque gradient centrifugation. The test was performed in triplicate (A Blank; B Test sample):

1. Dispense $2 \times 10^6$ to $3 \times 10^6$ cells into each of six test tubes; pellet cells by centrifugation at 300 $\times g$ for 10 minutes.
2. Add NRS (normal rabbit serum) 20 μl diluted 1:10 in PBS, incubate 60 minutes at 4° C.
3. Add 30 μl of ascites fluids (dilution $10^{-5}$ in 5% BSA) to each of 3 tubes.
   A. Control ascites fluid containing an IgG non-specific monoclonal antibody, non-reactive with PLF.
   B. CM-H9 monoclonal antibodies. Mix well and incubate at room temperature for 2 hours.
4. Wash cells twice with 10 ml RPMI-1640 by centrifugation at $300 \times g$ for 10 minutes at 4° C.
5. Add 0.1 μCi of $I^{125}$ rabbit anti-mouse IgG ($^{125}$-I Rabbit IgG 1μCi/μg) incubate 60 minutes at 4° C., wash twice with cold RPMI-1640 as in 4, count radioactivity.
   Positive test: Cpm A- CpmB<500; or Cpm A:Cpm B>1.6.

B. Radio Immuno Assay—2

After Stage 1, RIA—1, the test procedure is continued as follows: CM-H9 F(ab)$_2$ is obtained by peptic digestion of 4:1766). Control F(ab)$_2$ is similarly obtained from the nonspecific IgG (see control of RIA—1). The F(ab)$_2$ fragments thus obtained are used as follows:
Tube A: Control F(ab)$_2$ in 5% BSA in PBS (pH 7.2) 0.025% sodium azide.
Tube B: CM-H9 F(ab)$_2$ in 5% BSA in PBS (pH 7.2) 0.025% sodium azide.

Incubate for 60 minutes at room temperature, wash once with 2 ml of 1% BSA in PBS (pH 7.2); add $^{125}$I-labeled ligand to test tubes A and B (about 105 cpm); either $^{125}$I-labeled PLF or a complex of $^{125}$I-polyclonal anti-PLF with PLF. The complex is preformed at antigen/antibody molar ratios of 1:1 or up to 1:2, preincubated with each other at room temperature for 1 hour. Incubate the labeled ligand together with cells for 1 hour at room temperature, wash twice with 1% BSA in PBS (pH 7.2) to remove unbound labeled ligand and count. If B exceeds A the test is positive.

6.4.3. CYTOTOXIC ASSAY PROCEDURE

Test is performed in duplicates: (A) Control; and (B) Test Sample.
a. Suspend PBL at a density of $5 \times 10^6$ cells/ml in RPMI-1640
b. Place 150 μl of PBL into each of four 12×75 mm test tubes. Add ascites fluid (30 μl dilution $10^{-4}$): A. Control ascites fluid (2 tubes); B. CM-H9 (2 tubes). Incubate 45 minutes at 4° C.
c. Add rabbit complement (100 μl diluted 1:5 in PBS) and incubate 60 minutes at 37° C. with slow agitation.
d. Count viable cells with Trypan blue.

Positive Test: =

$$\frac{\text{No. viable cells in } A - \text{No. viable cells in } B}{\text{No. of viable cells in } A} \times 100 \geq 6\%$$

6.4.4. RESULTS: REACTIVITY OF CM-H9 MONOCLONAL ANTIBODY WITH LYMPHOCYTES IN CERTAIN DISEASES

Using the assays described above, the two monoclonal antibodies CM-H9 and CM-3 were used to screen serum and PBL obtained from patients with various diseases as well as disease-free subjects. The results presented in Table I below indicate that the two antibodies make possible rapid and convenient detection of malignancies of the breast and of Hodgkin's disease, and provide for differentiation of these from thalassaemia, which results in an increase of normal ferritin.

TABLE I

REACTIVITY OF PLF MONOCLONAL ANTIBODY WITH DIFFERENT PATIENT SAMPLES

| Source of Human Ferritin | Anti-PLF CM-H9 | Anti-Ferritin CM-3 |
|---|---|---|
| 1. Adult spleen (Thalassaemia) | − | + |
| 2. Normal serum | − | + |
| 3. Breast cancer (PBL) | + | + |
| 4. Breast cancer (serum) | + | + |
| 5. Hodkin's Disease (spleen) | + | + |
| 6. Benign breast disease (PBL) | − | − |
| 7. Benign breast disease-serum | − | + |

7. ISOFERRITINS IN HIV INFECTION: RELATION TO CLINICAL STAGE, CD8+ LYMPHOCYTE BINDING AND THE PATHOGENESIS OF AIDS

In the examples detailed infra, placental isoferritins (PLF) were found to be increased in sera of subjects infected with human immunodeficiency virus (HIV). PLF was quantified by use of a "sandwich" antigen capture ELISA employing two monoclonal antibodies. Individuals with lymphadenopathy, with or without symptoms suggestive of AIDS-related complex, had the highest serum levels, which declined with progressive immunodeficiency. Total (normal) ferritins, in contrast, increased progressively with stage of disease. PLF was found on the cell surface of a subset of CD8+ lymphocytes and appeared to block detection of the CD8 antigen by specific monoclonal antibodies. Elution of PLF from the cell surface, achieved by incubation with levamisole but not by culture medium alone, led to the unblocking of the CD8 determinant on these cells. Profiles of isoferritins in HIV infection may thus provide clues to prognosis. PLF, a physiologic down-regulator of hematopoiesis and cellular immunity, may be abnormally expressed via trans-activation by HIV gene products, and could play a role in the progressive immune deficiency, marrow suppression and HIV expression that lead to AIDS.

7.1. MATERIALS AND METHODS

7.1.1. Subjects

Sera from HIV seropositive patients were derived from material stored at −70° C. obtained during a previous study (Siegal, F.P., et al., 1986, J. Clin. Invest. 78:115-123), and from patients in an ongoing study. Patients were classified according to clinical stage with the modification that all subjects included were confirmed to be HIV seropositive. The stages were defined as follows: Stage A: HIV seropositive but without clinical manifestations or physical findings; B: lymphadenopathy and/or splenomegaly; C: clinical symptoms or findings related to ARC; D: Kaposi sarcoma, lymphoma, or CNS (central nervous system) disease but without systemic opportunistic infections; E: opportunistic infections defining AIDS by original Center for Disease Control (CDC) criteria (Center for Disease Control, Update on acquired immune deficiency syndrome (AIDS)-United States, 1982, Morbid. Mortal. Weekly Rep. 31:507-514). Sera were also obtained from 40 hematologically normal blood bank donors.

7.1.2. Isolation of Lynmphocytes

Peripheral blood mononuclear cells were isolated from fresh heparinized blood by Ficoll-Hypaque gradient density centrifugation.

7.1.3. Monoclonal Antibodies

Monoclonal antibodies (McAb) T4, T8 and T11, reactive with CD4+, CD8+, and CD2+ cells, respectively, directly conjugated to fluorescein or phycoerythrin, were obtained from Coulter Immunology (Hialeah, Fla.). CM-H9 McAb which defines human placental ferritin and has been shown to react exclusively with placental isoferritin and not with liver or spleen ferritins (Moroz, C., et al., 1985, Clin. Chim. Acta 148:111-118). CM-G8 McAb was produced against human placental isoferritin, but also reacts with human liver and spleen ferritins in addition to PLF (id.).

7.1.4. Flow Cytometry and Immunofluorescence Staining

CD4+, CD8+, and CD2+ cells were assayed by flow cytometry using a Coulter Epics 5 cell sorter modified for two color immunofluorescence. The lymphocytes were directly reacted with phycoerythrin conjugated T4 McAb, and with fluorescein-isothiocyanate conjugated T8 McAb or T11 McAb, according to the manufacturer's specifications.

7.1.5. Immunofluorescence Staining of Isoferritin on Lymphocyte Membranes Using CM-H9 McAb Lymphocytes were washed twice at room temperature with phosphate buffered saline (PBS), pH 7.2, containing 2% bovine serum albumin (BSA) and 0.01% sodium azide (PBS-BSA). Two aliquots, containing $1 \times 10^6$ mononuclear cells each, were incubated in 25 ul of diluted CM-H-9 McAb overnight at 4° C. A third aliquot, containing $1 \times 10^6$ cells, was incubated with 25 ul of mouse IgG (Coulter) as a negative control. After incubation, the mononuclear cells were washed three times in PBS-BSA, incubated with 25 ul fluorescein-conjugated F(ab')$_2$ fragments of goat anti-mouse IgG F(ab')$_2$ (diluted 1:2) (Capell) for 30 minutes at 4° C., and washed again three times in PBS-BSA.

After centrifugation, the washed cell pellets were suspended in 20 ul of PBS-BSA and examined on a microscope slide with a Leitz Orthoplan epifluorescence microscope, with an excitation wave length of 288 nm for quantitation of the CM-H9 McAb membrane stained lymphocytes. At least 400 lymphocytes were counted. Monocytes were morphologically identified by their large size and abundant granular cytoplasm, and were excluded from the count.

In some experiments, double staining of membrane isoferritin and CD4 antigen was carried out. Following the addition of CM-H9 McAb and FITC-anti-mouse F(ab')$_2$ IgG, the lymphocytes were washed twice with PBS-BSA and further incubated with phycoerythrin-anti-CD4 McAb (5 $\mu$l, Coulter) for 30 minutes at 4° C. The cells were washed twice with PBS and analyzed with a fluorescent microscope as described supra.

7.1.6. Immunofluorescence Staining of Isoferritin in Lymphocyte Cytoplasma Using CM-H9 McAb Lymphocytes ($1 \times 10^6$) were centrifuged onto pre-cleaned u microscope slides (Cytospin, Shandon Scientific), air dried for 5 minutes, and fixed in absolute methanol for 10 minutes at $-15°$ C. Cells were washed once in PBS for 5 minutes and incubated with CM-H9 McAb (50 $\mu$l) overnight in a moist chamber at room temperature. After the incubation, the slides were washed three times in PBS (5 minutes each) and further incubated with FITC-goat-anti-mouse F(ab')$_2$ (25 $\mu$l, Capell) for 30 minutes at room temperature. The cells were washed three times with PBS and examined for cytoplasmic fluorescence. Approximately $1-4 \times 10^3$ cells were counted per slide.

7.1.7. Levamisole Treatment of Mononuclear Cells

Levamisole (Sigma, St. Louis, Mo.) was added to whole blood or to isolated mononuclear cells to a final concentration of 40 $\mu$g/ml followed by incubation for 30 minutes at 37° C. as described by Ramot et al. (1976, N. Engl. J. Med. 294:809). The levamisole treated cells were then mixed with the different monoclonal antibodies, in preparation for flow cytometry and immunofluorescent staining as described above.

7.1.8. Quantitative Determination of Serum Isoferritin

Ferritin and placental isoferritin (PLF) were measured in the sera of 161 HIV infected patients and in the sera of 40 blood bank donors using a specific McAb ELISA as previously described (Moroz, C., et al., 1987, Exp. Hematol. 15:258-262). The "sandwich" ELISA method of Engval and Perlman (1972, J. Immunol. 109:129-132) as modified by Voller et al. (1975, Lancet 1:426), was used to develop the assays for ferritin and PLF.

In both the assay systems for ferritin and for PLF, the McAb CM-G8, which binds all isoferritins, was coupled to the solid phase as capture reagent. As previously shown, high concentration of normal ferritin did not compete with the binding of PLF to the solid phase (Moroz, C., et al., 1987, Exp. Hematol. 15:258-262). For detection of the captured antigen, alkaline phospatase-conjugated CM-G8 McAb was used for measurement of ferritin, and enzyme-conjugated CM-H9 McAb was used for measurement of PLF. The amount of placental ferritin that binds 2.5 pg of alkaline-phosphatase (AP)-conjugated CM-H9 McAb is defined as 10 units of PLF (10 U PLF).

7.1.9. Statistical Analyses

Data were analyzed with the statistical package EPI-STAT, run on an IBM-AT personal computer, using Student's t-test, correlation coefficient, linear regression and Chisquare.

7.2 RESULTS

7.2.1. Serum Levels of Ferritin and PLF In Patients With HIV Infection

The use of an ELISA specific for PLF enabled the measurement of PLF concentration, independently of the amount of total ferritin, in the serum of HIV infected patients and healthy blood bank donors. The results of such measurements are shown in FIG. 1A and Table II.

TABLE II

RELATIONSHIP OF PLF AND FERRITIN TO ARC AND AIDS

| SUBJECTS | Number of Subjects with Serum Ferritin Levels Indicated | | | |
|---|---|---|---|---|
| | <10 U/ml | >10 U/ml | $X^{2*}$ | P |
| Normal Control: | 36 | 4 | | |
| HIV Infected | | | | |
| A | 16 | 8 | 3.24 | 0.04 |
| B | 19 | 30 | 22.36 | $2.3 \times 10^{-6}$ |
| C | 8 | 17 | 21.09 | $4.4 \times 10^{-6}$ |
| D | 26 | 11 | 3.6 | 0.058 |
| E | 33 | 18 | 6.51 | 0.011 |

| SUBJECTS | Number of Subjects with Serum PLF Levels Indicated | | | |
|---|---|---|---|---|
| | <200 ng/ml | >200 ng/ml | $X^{2*}$ | P |
| Normal Control: | 37 | 3 | | |
| HIV Infected | | | | |
| A | 18 | 4 | 0.72 | 0.39 |
| B | 51 | 2 | 0.1 | 0.7 |
| C | 18 | 6 | 2.49 | 0.11 |
| D | 14 | 23 | 23.29 | $1.49 \times 10^{-6}$ |
| E | 17 | 37 | 32.55 | $<10^{-8}$ |

*Compared to normal control.

As shown in FIG. 1A, the mean concentration of PLF was $10 \pm 31.5$ U/ml in healthy donors. It is noteworthy that 70% of the sera tested contained no detectable PLF, with only 10% having concentrations higher than 10 U/ml (FIG. 1A, Table I). The most elevated concentrations of PLF ($25 \pm 25.3$ and $18.2 \pm 16$ U/ml), significaintly higher than normal ($p < 0.01$), were observed in patients at early stages of clinically manifested disease (stages B, C) (FIG. 1A). Also, in contrast to the results obtained with normal sera, 61-68% of these patients, sera contained more than 10 U/ml of PLF in their serum (FIG. 1A, Table II).

On the other hand, patients with more advanced HIV infection (stages D, E) had relatively lower mean serum levels of PLF ($7.8 \pm 11.7$, $9.7 \pm 14.7$), which were not significantly different than those of normal controls (FIG. 1A). Furthermore, only 29.7% and 3.53% of the patients with AIDS had more than 10 U/ml of serum PLF (FIG. 1A, Table II).

Figure 1A:
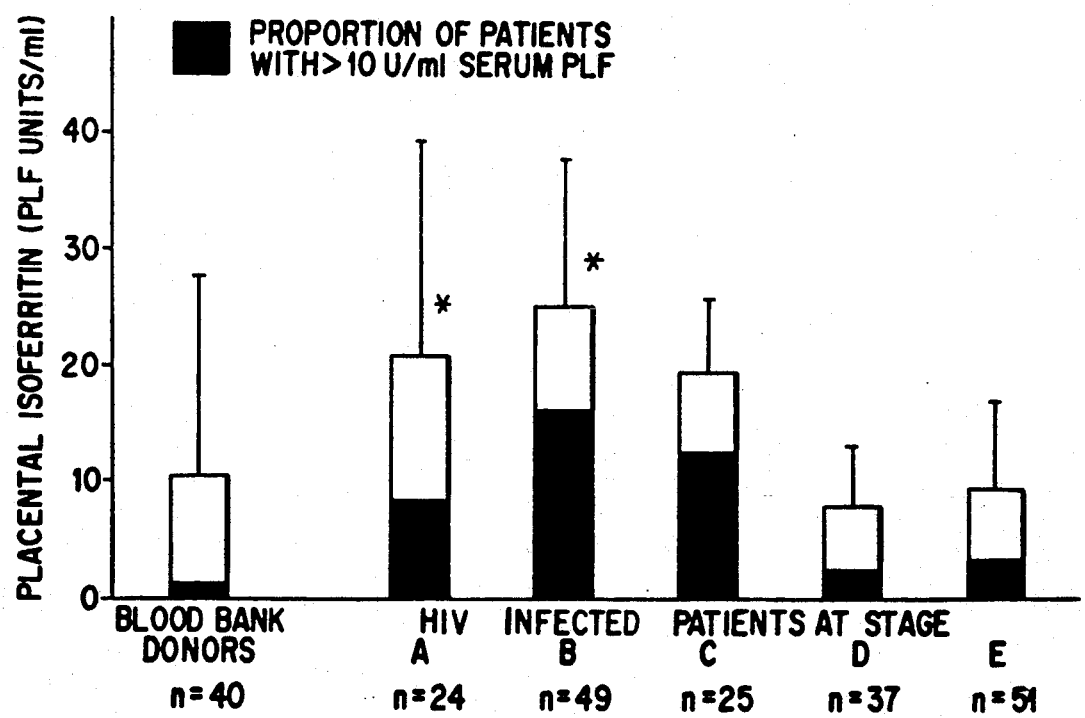

In contrast to the above results, the normal ferritin levels rose progressively as the disease progressed (FIG. 1B, Table II). Sixty-two and 68.5% of those with advanced disease (stages D, E) had more than 200 ng/ml of serum ferritin (FIG. 1B, Table II). Among HIV seropositive patients without clinical or physical signs (stage A), the mean level of PLF was slightly increased above normal to 20.7 ±34.2 U/ml, with 33% of the patients having more than 10 U/ml (FIG. 1A, Table II), which was not significantly different from that of normal controls. The total ferritin level was also not significantly differ from that of healthy donors (FIG. 1B, Table II).

7.2.2. Relationship of High Serum PLF and Normal Ferritin to Disease Progression Contingency table analysis of the individual results exhibited in FIG. 1 was carried out using a cutoff level of 10 U/ml for PLF (chosen because 90% of normal control levels were below this value) and 200 ng/ml of total ferritin (chosen because 92.5% of normal control levels were below this value). The results obtained revealed a statistically significant relationship between elevation of serum PLF level and the presence of relatively early stages of HIV infection (for stages B and C, $p = 23 \times 10^{-6}$, and $p = 4.4 \times 10^{-6}$, respectively), whereas an elevation in the total ferritin level was highly associated with advanced disease (for stages D and E, $p = 1.49 \times 10^{-6}$, and $p < 10^{-8}$, respectively) (Table II).

Correlations carried out between the number of CD4+ and CD8+ cells in the patients, peripheral blood and serum levels of PLF and total ferritin, revealed a positive relationship (correlation coefficient of 0.17, $p < 0.02$) between the number of circulating CD4+ cells and the level of serum PLF. PLF levels decreased with decreasing numbers of circulating CD4+ cells. It is noteworthy that the majority of patients with the most advanced disease (stages D, E) which had undetectable PLF, had very low or undetectable CD4+ cells.

We next determined the ratio of the serum PLF level (in those with detectable amounts) to CD4+ lymphocyte count (FIG. 2). Interestingly, the AIDS patients (stage E) had a significantly higher ratio of PLF U/CD4+ cell ($p = 7.89 \times 10^{-3}$) than was observed in patients at early stages (B, C) of the disease (FIG. 2). No significant correlation was found between PLF levels and the number of CD8+ cells. These results are consistent with the idea that PLF is produced and secreted by CD4+ cells.

In contrast, a negative correlation (coefficient of $-0.3$, $p < 0.0001$) was found between the concentration of normal ferritin and the number of both CD4+ and CD8+ lymphocytes. The increase in total ferritin paralleled the progressive lymphoid depletion, suggesting that the principal source of normal ferritin is not HIV infected lymphocytes.

7.2.3. Cell Surface Antigens of Lymphocytes From HIV Infected Patients

Since it was previously shown that PLF binds to T cells and blocks sheep erythrocyte rosettes (Moroz et al., 1977, Clin. Exptal. Immunol. 29:30-35; Giller et al., 1977, Cancer Immunol Immunother. 3:101-105) we investigated the possibility that PLF bearing lymphocytes could be identified in HIV infected patients. As shown in FIG. 3, 3-28% of the circulating lymphocytes from HIV infected patients at various stages (A-E) reacted with CM-H9 McAb, and thus were exhibiting surface PLF. A small proportion (0.2-2.5%) of the lymphocytes also exhibited cytoplasmic PLF (FIG. 3).

As expected, the T cell subset ratio was reversed in HIV infected patients (Table III).

TABLE III

CELL SURFACE ANTIGENS IN HIV INFECTED PATIENTS AND NORMAL SUBJECTS

| Lymphoid Cells | Percentage of Lymphoid Cells Stained (mean ± SD) | |
|---|---|---|
| | Healthy Donors (n = 35) | HIV-Infected[a] (n = 12) |
| T4+ | 49.5 ± 9.4 | 24.7 ± 14.5 |
| T8+ | 22.9 ± 6.3 | 39.8 ± 13.8 |
| T11+ | 76.2 ± 9.7 | 81.8 ± 9.0 |
| T11+T4−T8−[b] | 6.9 ± 7.8 | 20.1 ± 8.2 |
| PLF+[c] | 0.78 ± 1.17 | 15.2 ± 6.4 |

[a]Number of HIV-infected patients at the following stages: A = 1, B = 2, C = 6, D = 1, E = 2.
[b]Percentage of T11+ cells less the sum of the percentages of T4+ and T8+ cells. The results shown differ significantly as measured by the Student's T-test ($p = 9.76 \times 10^{-6}$).
[c]$p < 10^6$. For PLF staining, 15 normal donors of the 35 donors used for T cell subset quantitation were analyzed. For all HIV-infected patients, all membrane markers (including PLF) were assayed simultaneously.

Lymphocytes identified by McAbs T4 and/or T8, accounted for a signifcantly smaller proportion of those stained by T11 McAb in HIV infected patients compared to normal subjects (Table III). This observation revealed the existence of an expanded T11+ population which did not react with either T4 or T8 monoclonal antibody (T11+T4−T8−) This population is significantly higher ($p = 9.76 \times 10^{-10}$) in HIV infected patients than in normal controls (6.9±7.8%). This subpopulation (T11+T4−T8−) in HIV infected patients (where it is present at approximately 13.2% more than in normal subjects) is similar to the size of the population identified as PLF positive (15.16±6.39%) (Table III) in the same HIV-infected subjects.

Further experiments were carried out to elucidate which of the T cell subsets bore surface PLF reactive with the CM-H9 McAb. Dual labeling for CD4 and PLF on lymphocytes from two subjects with late stage HIV infection (Table IV), indicated that PLF is associated mainly with non-CD4+ lymphocytes.

TABLE IV

DOUBLE MEMBRANE IMMUNOSTAINING OF LYMPHOCYTES FROM AIDS PATIENTS USING ANI-T4, AND ANTI-PLF (CM-H9) MONOCLONAL ANTIBODIES

| Lymphocyte | PERCENTAGE LYMPHOCYTES STAINED | |
|---|---|---|
| | Patient No. 1 | Patient No. 2 |
| T4+ | 42 | 28 |
| PLF+ | 13 | 13 |
| T4+PLF+ | 0 | 5 |
| NOT STAINED | 48 | 54 |

7.2.4. The Effect of Levamisole on Cell Surface Antigens of Lymphocytes From HIV Infected Patients When the peripheral blood lymphocytes of HIV infected concomitant phenomena occurred. The number of cells stained with the T8 McAb increased by about 20%, while the number of CM-H9 positive lymphocytes (PLF coated) decreased by about 15% (FIG. 4). The number of T4+ stained cells did not change following levamisole treatment (FIG. 4). The number of T11⁻ (CD2⁻) cells also did not change following levamisole treatment. These results, taken together with the results obtained following dual labeling with the CD4 and PLF specific McAb, suggest that levamisole caused shedding of membrane bound PLF, unmasking CD8 determinants on a proportion of CD8⁺CD2⁻ T cells. Parallel incubation in tissue culture medium did not have an equivalent effect (FIG. 4).

8. ISOFERRITINS IN PATIENTS WITH LYMPHOPROLIFERATIVE DISEASES

In the examples detailed below, serum levels of total ferritin and PLF were measured in healthy individuals and in patients with lymphoproliferative disease and multiple myeloma. The majority of normal subjects were deficient in PLF in the serum. Increased serum levels of PLF were observed in patients with Hodgkin's lymphoma and non-Hodgkin's lymphoma of low and intermediate grades, as well as in patients with acute lymphocytic leukemia (ALL). Total ferritin was also elevated in these patients. Chronic lymphocytic leukemia (CLL) and multiple myeloma patients exhibited normal levels of common serum ferritin, whereas PLF in the serum was lacking (See also, Moroz et al., 1987, Exp. Hematol. 15:258-262).

8.1. MATERIALS AND METHODS

8.1.1. Subjects

Serum samples were obtained from 40 blood bank donors who were hematologically normal, and from 70 patients with various lymphoproliferative disorders, as well as from patients with multiple myeloma. There were 20 patients with chronic lymphocytic leukemia (CLL), 18 patients with non-Hodgkin's lymphoma, 15 with Hodgkin's disease, five with multiple myeloma, and two with ALL. Of the patients with non-Hodgkin's lymphoma of intermediate grade, two had peripheral blood involvement. A patient with non-Hodgkin's lymphoma and the two patients with ALL received six packages of packed red blood cells each prior t ferritin determinations. Serum samples were taken during one of the followup periods, at diagnosis, and during treatment or active disease. Only in patients with Hodgkin's disease was serum also taken during remission. The classification of lymphoma was made according to a working formulation (Krueger et al., 1983, Cancer 52:833).

8.1.2. Monoclonal Antibodies

McAbs CM-G8 and CM-H9 were produced against human PLF as previously described in Section 6 et seq. supra, (see also, Moroz et al., 1985, Clin. Chim. Acta 148:111). McAbs were obtained from ascites fluid after precipitation with 50% saturated ammonium sulfate solution. The PLF used for the standard was obtained after purification on a diethylaminoethyl (DEAE)-cellulose column, as described above (see also, Moroz et al., 1985, Clin. Chim. Acta 148:111). Liver-ferritin standards were obtained from MELISA ferritin kits (Elias Medizintechnik, Freiburg, FRG). The amount of PLF that bound 2.50 pg of alkaline phosphatase (AP)-conjugated CM-H9 McAb was considered to be 10 U of PLF.

8.1.3. Quantitative Determinations of Ferritin

MELISA commercial ferritin kits were obtained from Elisa Medizintechnik and were used according to the manufacturer's instructions. In this kit, the binding of perioxidase-conjugated polyclonal antihuman liver ferritin is measured.

8.1.4. Monoclonal Antibody Elisa for PLF and Common Isoferritins

The enzyme linked immunosorbent assay (ELISA) of Engval and Perlmann (1972, J. Immunol. 109:129), with the modification of Voller et al. (1975, Lancet 1:426), was used in the formating of an ELISA for measuring the serum liver ferritin and PLF isoforms (McELISA type A and McELISA type B, reprectively). In both assays, the McAb CM-G8, which binds to all ferritins, was coupled to the solid phase. For the second site, McAb-enzyme-conjugate reaction, CM-G8 McAb, was used in McELISA type A and CM-H9 McAb was used in McELISA type B.

The type A and B McELISAs were performed as follows: the wells of microtiter plate were coated with 150 μl CM-G8 McAb (100 μg/ml phosphate-buffered saline [PBS], pH 7.2) and incubated overnight at 4° C. The plate was washed three times with PBS-Tween (PBS and 0.05% Tween 20) and shaken dry.

Test sera (100 μl) diluted 1:2 with McELISA type A and 1:4 with McELISA type B in PBS-Tween 0.025% were added in duplicate to the wells. Serum diluent and ferritin standards were also added in duplicate. A serum sample with an elevated ferritin concentration was placed in the diluent to determine recovery at high dilution. The plates were incubated at 4° C. for 1 hour in McELISA A and overnight in McELISA B, washed three times with PBS-Tween, and 100 μl of AP-McAb conjugate (0.4 μg) was added to each well. The plate was incubated for an additional 120 minutes at room temperature and washed again three times. The enzyme buffer, pH 8.0, and 0.5 mmol $MgCl_2$) was added and the reaction stopped after 10-30 minutes by the addition of 0.05 ml of 2 M NaOH. The amount of colored product was measured by absorbance at 405 nm.

8.2. RESULTS

The results described below demonstrate that serum PLF levels are elevated in patients with lymphoproliferative diseases such as acute lymphocyte leukemia, active Hodgkins lymphoma and non-Hodgkins lymphoma of low and intermediate grade.

8.2.1. Evaluation of Liver Ferritin Standard by Different ELISAs

Liver ferritin standards obtained from MELISA commercial kits were assayed by the new McELISA type A and compared to those from the commercial MELISA kit. The binding pattern of liver ferritin at concentrations ranging from 15 to 500 ng/ml was similar in both assay systems.

Serum samples containing low and high ferritin levels, supplied by MELISA kits, were assayed by the two systems. The concentrations of ferritin at the low-control level were 70 ng/ml and 57 ng/ml in McELISA type A and the MELISA kit, respectively. Both values were within the range specified by the MELISA manufacturers (40-70 ng/ml). The concentration of ferritin at the high-control level was 500 ng/ml as assayed by both systems (manufacturer's given range, 350-500 ng/ml).

In addition, correlations were made between the ferritin results obtained by the McELISA type A and MELISA assays: 22 sera from normal donors, covering the range 10-150 ng/ml, and 21 sera from cancer patients, covering the range 50-400 ng/ml, were tested.

The correlation coefficient for the normal range was 0.98, with the regression equation y=1.05±8.1; for the higher range it was 0.967, with y=1.37 ±21.09.

The results demonstrate that the McELISA type A, using AP-conjugated CM-G8 McAb, is suitable for the quantitative determination of normal levels of liver-type ferritin in the serum. However, in high-range ferritin determinations, higher quantities were measured by the McELISA type A than by the MELISA.

8.2.2. Binding of Placenta and Liver Ferritins to CM-G8 and CM-H9 MCABS

Both placenta and liver ferritins were measured in McELISA type A using a conjugate of AP-CM-G-8 McAb. Similar patterns of binding of these two isoferritins were observed at concentrations ranging from 30 to 800 ng/ml. The results indicated that our newly developed McELISA type A is suitable for the measurement of both liver and PLF isoferritins. By contrast, a specific determination of PLF was possible only when the McELISA type B was used.

The binding of AP-conjugated CM-H9 McAb to PLF in McELISA type B was linear at concentrations ranging from 2.5 to 20 units, whereas liver ferritin at concentrations ranging from 100 to 800 ng/ml did not bind AP-conjugated CM-H9 McAb. These results exhibit the specificity of McELISA type B for the detection of PLF.

8.2.3. Isoferritins in the Serum of Healthy Individuals and Patients With Lymphoproliferative Diseases The results of the assay for isoferritins obtained from healthy individuals and in patients with lymphoproliferative disease are presented in Table V.

TABLE V
ISOFERRITINS IN HEALTHY INDIVIDUALS AND IN PATIENTS WITH LYMPHOPROLIFERATIVE DISEASES AND MULTIPLE MYELOMA

| Sources and diagnosis | n | Ferritin (ng/ml) | PLF (U/ml) |
|---|---|---|---|
| Blood bank donors | 40 | 85.3 ± 65.9 | 8.1 ± 14.8 |
| Male | 24 | 108.0 ± 58.0 | 10.0 ± 10.0 |
| Female | 16 | 50.3 ± 59.8 | 4.5 ± 7.7 |
| CLL[a] | 20 | 66.3 ± 33.0 | 6.3 ± 13.5 |
| ALL[b] | 2 | 600.0 ± 0** | 140.0 ± 84.8* |
| Multiple myeloma | 5 | 68.5 ± 39.2 | 0 |
| Hodgkins lymphoma | | | |
| Active | 5 | 359.0 ± 236.0** | 47.0 ± 43.0* |
| Remission | 10 | 95.1 ± 46.7 | 15.3 ± 19.3 |
| Non-Hodgkin's lymphoma | | | |
| Low grade | 7 | 218.3 ± 186.9* | 97.1 ± 39.0** |
| Intermediate | 9 | 272.8 ± 180.8** | 41.9 ± 35.8** |
| High grade | 2 | 380 ± 311 | 6 ± 8.5 |

[a]Chronic lymphocytic leukemia.
[b]Acute lymphocytic leukemia. Significantly different from blood bank donors by Students t-test: *p < 0.025; **p < 0.005.

The mean concentration of ferritin measured in the sera of healthy individuals by McELISA type A was 85.3±65.9 ng/ml (Table V). The mean ferritin concentration was higher in males (108±58 ng/ml) than in females (50.3±59.8 ng/ml) (Table V). Significantly higher ferritin levels (p<0.025) were measured in the sera of patients suffering from the following malignant diseases: Hodgkin's lymphoma (359±236 ng/ml) and non-Hodgkin's lymphona of low and intermediate grades (218.3±186.9 and 272.8±180.88 ng/ml, respectively), as well as in two patients with ALL (600±0 ng/ml). Sera of patients with Hodgkin's lymphoma in remission showed mean ferritin levels (95.1±46.7 ng/ml) similar to those of healthy individuals. Patients with CLL and multiple myeloma exhibited normal ferritin levels (66.3±33 and 68.5±39.2 ng/ml, respectively). The individual ferritin concentrations measured with McELISA type A are shown in FIG. 5.

The mean serum concentration of PLF measured by McELISA type B in the serum of healthy individuals was 8.1±14.8 U/ml (Table V). Although higher concentrations were measured in male (10±10 U/ml) than in female (4.5±7.7 U/ml) sera, these were not statistically significant. It is noteworthy that 70% of the sera tested contained no detectable PLF. Elevated concentrations of PLF, significantly higher than normal (p<0.025), were measured in the sera of patients with Hodgkin's disease (47±43 ng/ml) and with non-Hodgkin's lymphoma of low and intermediate grades (97.1±39 and 41.9±35.8 U/ml, respectively). Patients with Hodgkin's lymphoma in remission had serum PLF levels not significantly different from those of healthy individuals (15.3±19.3 U/ml). High PLF levels were also measured in two patients with ALL (range 80-200 U/ml). No or very low PLF concentrations were found in the sera of patients with multiple myeloma (0) and CLL (6.3±13.5 U/ml), and 85% of the CLL patient's sera were completely negative. The individual distributions of PLF serum concentrations are presented in FIG. 6.

9. ISOFERRITINS IN AUTOIMMUNE CONDITIONS

Serum levels of PLF were measured retrospectively from stored samples derived from patients diagnosed with different autoimmune conditions. Results shown in FIG. 8 indicate that serum PLF levels were elevated in patients diagnosed as having multiple sclerosis, myasthenia gravis, and rheumatoid arthritis. Each of these autoimmune conditions are characterized by immunodeficiency.

10. DEPOSIT OF HYBRIDOMAS

The following hybridomas have been deposited with the Collection Nationale de Cultures de Microorganisms of the Institute Pasteur in Paris, France and received the accession number indicated:

| Hybridoma | Accession No. |
|---|---|
| CM-H9 | I-256 |

The present invention is not to be limited in scope by the hybridomas deposited or the embodiments disclosed in the examples which are intended as an illustration of one aspect of the invention, and any hybridoma and method which are functionally equivalent are within the scope of this invention. Indeed, various modifications of the invention in addition to those shown and described herein will become apparent to those skilled in the art from the foregoing description. such modifications are intended to fall within the scope of the appended claims.

What is claimed is:

1. A method for the prognosis and staging of acquired immunodeficiency associated with HIV infection, comprising:

(a) obtaining a serum sample from a patient; and (b) measuring the concentration of placental isoferritin and adult ferritin in the serum sample, in which (i) an elevated serum concentration of placental isoferritin and a normal serum concentration of adult ferritin in the sample indicates early stage disease, whereas, (ii) a normal serum concentration of placental isoferritin and an elevated serum concentration of adult ferritin in the sample indicates late stage disease.

2. The method according to claim 1 in which the concentration of placental isoferritin in the sample is measured by an immunoassay using an antibody specific for placental isoferritin which does not cross react with adult ferritin, comprising the steps of:
   (a) contacting the sample with the antibody specific for placental isoferritin; and
   (b) measuring the amount of the antibody which binds to the sample,
in which the amount of the antibody bound to the sample correlates with the amount of placental isoferritin in the sample.

3. The method according to claim 3 in which the antibody comprises a monoclonal antibody produced by hybridoma cell line CM-H9 as deposited with the Collection Nationale de Cultures de Microorganisms, having accession number I-256.

4. The method according to claim 3 in which the concentration of placental ferritin is measured in units, in which 10 units is defined as the amount of placental isoferritin that binds 2.5 picograms of monoclonal antibody CM-H9.

5. The method according to claim 2 in which the antibody specific for placental isoferritin is configured in a sandwich immunoassay system comprising:
   (a) contacting the sample with an immobilized antibody specific for placental isoferritin so that placental isoferritins in the sample are captured on the immobilized phase;
   (b) removing all unbound sample from the immobilized phase;
   (c) adding a conjugate to the immobilized phase which conjugate comprises a signal-generating component bound to an antibody specific for placental isoferritin;
   (d) removing all unbound conjugate from the immobilized phase; and
   (e) measuring the amount of conjugate which binds to the immobilized phase in which the amount of conjugate bound to the immobilized phase correlates with the amount of placental isoferritin present in the sample.

6. The method according to claim 5 in which the antibody specific for placental isoferritin comprises a monoclonal antibody produced by hybridoma cell line CM-H9 as deposited with the Collection Nationale de Cultures de Microorganisms, having accession number I-256.

7. The method according to claim 1 in which the concentrations of placental isoferritin and adult ferritin in the sample are measured by an immunoassay using at least two antibodies comprising the steps of
   (a) contacting the sample with
      (i) a first antibody specific for placental isoferritin which does not cross react with adult ferritin and
      (ii) a second antibody which reacts with adult ferritin;
   (b) measuring the amount of the first antibody and the amount of the second antibody which binds to the sample,
in which the amount of the first antibody bound to the sample correlates with the amount of placental isoferritin present in the sample, and the amount of the second antibody bound to the sample correlates with the amount of adult ferritin present in the sample.

8. The method according to claim 7 in which the antibodies are configured in a sandwich immunoassay comprising:
   (a) contacting the sample with an immobilized second antibody which cross reacts with both placental isoferritin and adult ferritin so that all isoforms of ferritin in the sample are captured on the immobilized phase;
   (b) removing all unbound sample from the immobilized phase;
   (c) adding a conjugate to the immobilized phase, which conjugate comprises a signal-generating component conjugated to either
      (i) the first antibody which is specific for placental isoferritin; or
      (ii) the second antibody which cross reacts with both placental isoferritin and adult ferritin;
   (d) removing all unbound conjugate from the immobilized phase; and
   (e) detecting the amount of conjugate which bound to the immobilized phase,
in which (i) the amount of first antibody conjugate bound to the immobilized phase correlates with the amount of placental isoferritin present in sample, and (ii) the amount of second antibody conjugate bound to the immobilized phase correlates with the amount of adult ferritin present in the sample.

9. The method according to the claim 7 or 8 in which
   (a) the first antibody comprises a monoclonal antibody produced by hybridoma cell line CM-H9 as deposited with the Collection Nationale de Cultures de Microorganisms, having accession number I-256; and
   (b) the second antibody comprises a monoclonal antibody produced by hybridoma cell line CM-G8, which antibody cross reacts with both placental isoferritin and with adult ferritin.

* * * * *

UNITED STATES PATENT AND TRADEMARK OFFICE
CERTIFICATE OF CORRECTION

PATENT NO. : 5,120,640
DATED : June 9, 1992
INVENTOR(S) : Chaya Moroz, et. al

It is certified that error appears in the above-indentified patent and that said Letters Patent is hereby corrected as shown below:

On the Title page, item [76] inventors: insert "Chaya Moroz, 40 Yehuda-Hanasi St, Tel-Aviv, Israel, 69393; S. Leslie Misrock, 74 Hilltop Dr., N.Y. 10514"-- instead of Chaya Moroz, 40 Yehuda-Hanasi St, Tel-Aviv,Israel, 69393; Sol L. Misrock, 74 Hilltop Dr., Chappaqua, N.Y. 10514--.

Signed and Sealed this

Seventh Day of September, 1993

Attest:

BRUCE LEHMAN

*Attesting Officer*     *Commissioner of Patents and Trademarks*